US010947383B2

(12) United States Patent
Huggins et al.

(10) Patent No.: US 10,947,383 B2
(45) Date of Patent: Mar. 16, 2021

(54) AQUEOUS SILICONE POLYMER COMPOSITIONS

(71) Applicant: Momentive Performance Materials GmbH, Leverkusen (DE)

(72) Inventors: John Huggins, Leverkusen (DE); Roland Wagner, Bonn (DE); Petra Kudla, Cologne (DE)

(73) Assignee: Momentive Performance Materials GmbH, Leverkusen (DE)

( * ) Notice: Subject to any disclaimer, the term of this patent is extended or adjusted under 35 U.S.C. 154(b) by 87 days.

(21) Appl. No.: 16/225,576

(22) Filed: Dec. 19, 2018

(65) Prior Publication Data
US 2019/0194457 A1 Jun. 27, 2019

(30) Foreign Application Priority Data
Dec. 21, 2017 (EP) .................................. 17209360

(51) Int. Cl.
| | | |
|---|---|---|
| *A61Q 11/00* | (2006.01) | |
| *C08L 83/04* | (2006.01) | |
| *C08K 3/013* | (2018.01) | |
| *C08K 5/053* | (2006.01) | |
| *C08K 5/06* | (2006.01) | |
| *C08K 5/13* | (2006.01) | |
| *A61K 8/892* | (2006.01) | |
| *A61K 8/34* | (2006.01) | |
| *A61K 8/898* | (2006.01) | |
| *A61K 8/891* | (2006.01) | |
| *A61Q 5/02* | (2006.01) | |
| *C11D 3/39* | (2006.01) | |
| *A61L 2/18* | (2006.01) | |
| *C08K 5/00* | (2006.01) | |

(52) U.S. Cl.
CPC ............... *C08L 83/04* (2013.01); *A61K 8/34* (2013.01); *A61K 8/345* (2013.01); *A61K 8/891* (2013.01); *A61K 8/892* (2013.01); *A61K 8/898* (2013.01); *A61Q 5/02* (2013.01); *A61Q 11/00* (2013.01); *C08K 3/013* (2018.01); *C08K 5/053* (2013.01); *C08K 5/06* (2013.01); *C08K 5/13* (2013.01); *C11D 3/394* (2013.01); *A61K 2800/524* (2013.01); *A61L 2/18* (2013.01); *C08K 5/005* (2013.01); *C08L 2201/52* (2013.01); *C08L 2201/54* (2013.01)

(58) Field of Classification Search
None
See application file for complete search history.

(56) References Cited

U.S. PATENT DOCUMENTS

| | | | | |
|---|---|---|---|---|
| 5,641,480 A | * | 6/1997 | Vermeer ............... | A61K 8/046 424/70.1 |
| 5,653,970 A | * | 8/1997 | Vermeer ............... | A61Q 19/00 424/70.24 |
| 6,620,418 B1 | | 9/2003 | Ogawa et al. | |
| 2006/0193818 A1 | * | 8/2006 | Southall ............... | A61K 8/41 424/74 |
| 2006/0239949 A1 | * | 10/2006 | Mohammadi ......... | A61K 8/891 424/70.12 |
| 2006/0239950 A1 | * | 10/2006 | Mohammadi ......... | A61K 8/31 424/70.12 |
| 2007/0009446 A1 | * | 1/2007 | Romero ................ | A61K 8/046 424/47 |
| 2007/0166267 A1 | * | 7/2007 | Majewski .............. | A61K 8/64 424/70.14 |
| 2009/0202581 A1 | * | 8/2009 | Schlemer .............. | A61K 8/492 424/195.16 |
| 2011/0229424 A1 | * | 9/2011 | Schumann ............. | A61K 8/06 424/62 |
| 2012/0152149 A1 | | 6/2012 | Mijolovic et al. | |
| 2016/0089319 A1 | * | 3/2016 | Pollefliet ............. | A61K 49/0008 424/9.2 |
| 2017/0049691 A1 | * | 2/2017 | Weisman .............. | A61K 8/34 |
| 2018/0133140 A1 | * | 5/2018 | Zecchino ............. | A61K 8/362 |
| 2018/0318247 A1 | * | 11/2018 | Cohen .................. | A61K 8/34 |

FOREIGN PATENT DOCUMENTS

| | | |
|---|---|---|
| DE | 102012212281 B3 | 10/2013 |
| DE | 202013104382 U1 | 11/2013 |
| EP | 1040757 A2 | 10/2000 |
| JP | 2003286153 A | 10/2003 |
| JP | 2004182639 A | 7/2004 |
| WO | 9318714 A1 | 9/1993 |
| WO | 2008119841 A2 | 10/2008 |
| WO | 2011002929 A1 | 1/2011 |
| WO | 2011023582 A2 | 3/2011 |
| WO | 2011047420 A1 | 4/2011 |

OTHER PUBLICATIONS

Datasheet for Diocide, 5 pages, 2020. (Year: 2020).*
European Search Report from European Applicaton No. EP17209360 dated Apr. 24, 2018.

* cited by examiner

*Primary Examiner* — Robert S Loewe
(74) *Attorney, Agent, or Firm* — Joseph S. Ostroff

(57) ABSTRACT

The present invention relates to aqueous compositions comprising one or more silicones and a synergistic combination of anti-microbiological agents, to a process for preparing the aqueous compositions, and to the use of said aqueous compositions, in particular, for the manufacture of home care articles, household cleansing articles, fabric articles, cosmetic articles, hygienic articles, medical articles etc.

23 Claims, No Drawings

AQUEOUS SILICONE POLYMER COMPOSITIONS

This application claims priority to European Patent Application No, 17209360.1 filed on Dec. 21, 2017, the entire contents of which are incorporated herein by reference.

FIELD OF INVENTION

The present invention relates, in particular, to aqueous compositions comprising one or more silicones and a synergistic combination of anti-microbiological agents. The present invention is also concerned with a process for preparing the aqueous compositions, the use of said aqueous compositions, in particular, for the manufacture of homecare articles, household cleansing articles, fabric articles, cosmetic articles, hygienic articles, medical articles etc., and the articles comprising the aqueous compositions. Furthermore the present invention relates to a method for the cosmetic, hygienic, medical or cleansing treatment using said articles, the use of the combination of anti-microbiological agents for preserving aqueous compositions comprising at least one silicone against microorganism, such as bacteria, yeasts, and particularly molds and fungi, and a preservative composition comprising the combination of anti-microbiological agents.

BACKGROUND OF THE INVENTION

Silicone polymers, including polydimethylsiloxanes, aminosilicones, silicone copolyols, quaternized silicones or quaternized silicone copolyols, are widespread ingredients used in cosmetic, hygienic, medical or household articles for various purposes such as cleaning applications. These polymers are often incorporated into the final article as an aqueous composition such as an oil-in-water emulsion or a microemulsion. To avoid spoiling, these aqueous compositions are commonly protected against microbiological growth by use of preservatives.

Commonly cosmetic and other articles use synthetic preservatives such as parabens and isothiazolinones among others. Such preservatives are known to have certain toxicological properties that can lead to limitations in use. Thus, many manufacturers of cosmetic articles would like to avoid the use of these synthetic preservatives and instead use substances that are of natural origin or nature-like and are toxicologically acceptable.

Alcohols are widespread ingredients used in cosmetic, hygienic, medical or household articles for various purposes such as cleaning applications and are considered to be acceptable alternatives to synthetic preservatives. Known anti-microbiological alcohol preservatives for cosmetics include, among others, the aromatic alcohols 2-phenoxyethanol, benzyl alcohol and 3-phenyl-1-propanol. These aromatic alcohols, if used alone in acceptable amounts of 1.0 weight % or less, do not as a rule provide adequate antimicrobial effectiveness in compositions comprising silicone polymers.

There is consequently a need for preservatives for use in aqueous composition of silicones and the corresponding cosmetic hygienic, medical or household formulations, such as cleaning formulations, incorporating such silicones, that are of natural origin or nature-like, toxicologically acceptable and also exhibit good antimicrobial effectiveness. A number or approaches to this problem have been described.

Some known combinations of antimicrobial components do not provide adequate microbiological protection. The use of the benzyl alcohol derivatives in cosmetic or other articles for application to the human skin is not desirable, in particular for children, and is considered to be detrimental for health reasons. 2-Phenoxyethanol, 2-phenylethanol and 3-phenyl-1-propanol are preferred antimicrobiological agents in cosmetic, hygienic, medical or household articles such as cleansing articles. In cosmetic articles intended for application to the skin, the use of these agents is restricted to less than or equal to 1.0% of the total composition. The use of tetraalkylammonium compounds together with 1,2-alkanediols is not desirable as this may lead to skin irritation. Parabens, isothiazolinones and tetraalkylammonium compounds are considered to have unacceptable toxicological properties, in particular for leave-on compositions such as those used in skin care. These antimicrobiological agents are undesirable as they may result in skin irritation or even sensitization in some people, in particular children.

It is recognized that specific microorganisms, such as *Aspergillus niger, Aspergillus brasiliensis, Penicillium funiculosum, Penicillium pinophilum* and *Pseudomonas aeruginosa*, are particularly difficult to control with low amounts of antimicrobiological agents. It is also known that controlling microbiological growth in aqueous compositions of the inventive silicon polymers is particularly difficult. Without being bound by theory, it is believed that the silicone oil-to-water interface in these aqueous compositions is particularly advantageous for the growth of microorganisms, at least in part, due to the relatively high oxygen solubility of the silicone polymers. It is also desirable to keep the total level of the antimicrobiological agents required for adequate control at or below 10%, preferably 5% or less, most preferably 3 weight % or less of the total composition. It has been found that use of 1,2-alkanediols, alone, or in combination with up to 1.0% of aromatic alcohols, such as 2-phenoxyethanol and 3-phenyl-1-propanol, cannot adequately control these difficult microorganisms in aqueous compositions of the inventive silicone polymers at low levels of use. There is thus a need for toxicologically acceptable agents that can effectively control microbiological growth in aqueous compositions of silicone polymers.

SUMMARY OF THE INVENTION

Accordingly, it was an object of the present invention to overcome at least one, preferably all of the disadvantages known in the prior art. Especially, it was an object of the present invention to provide a microbiologically stable aqueous composition comprising one or more silicone polymers such as those taken from the list consisting of polydimethylsiloxanes, aminosilicones, silicone copolyols, quaternized silicones or quaternized silicone copolyols, and antimicrobiological agents, that are toxicologically acceptable and also capable of controlling bacteria, yeasts, and particularly molds and fungi at low levels of use. It was also an object of this invention to provide a process for incorporating the inventive antimicrobiological agents into the aqueous composition.

Microbiologically stable aqueous compositions of the silicones in accordance with the invention include in particular compositions comprising sufficient antimicrobiological agents as are found to be free of microbes that grow colonies on agar after inoculation with living microbes and incubation for a number of days. The incubation time required to kill all the inoculation microbes is defined at the "days to destruction" of such microbes. Preferred are compositions for which the number of days to destruction is shortest.

Accordingly, the present invention provides an aqueous composition comprising of one or more silicones, such as silicone polymers which are selected for example from the list consisting of polydimethylsiloxanes, aminosilicones, silicone copolyols, quaternized silicones or quaternized silicone copolyols, and a) at least one compound of the general formula (1)

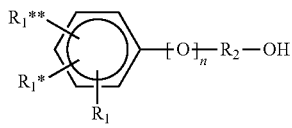

(1)

wherein
n is 0 or 1,
$R_1$, $R_1^*$ and $R_1^{**}$ are independently selected from the group consisting of hydrogen, a linear or branched C1-C9 alkyl group, and a linear or branched C1-C9 alkyloxy group, and
$R_2$ is a linear or branched divalent C2-C5 alkyl group,
and b) at least one compound selected from the group consisting of the general formulae (2) and (3)

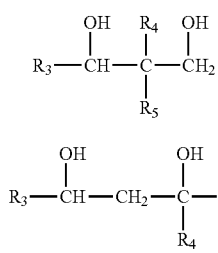

wherein compounds (2) and (3) each have 5 to 22 carbon atoms, preferably 6 to 22 carbon atoms, and wherein
$R_3$ is selected from the group consisting of hydrogen, a linear or branched C1 to C12 alkyl group, a linear or branched C1 to C12 alkylaryl group, an aryl group, a linear or branched C1 to C12 alkyloxy group, a linear or branched 01 to C12 alkylaryloxy group, and an aryloxy group, and
$R_4$ and $R_5$ are the same or different and are selected from the group consisting of a linear or branched C1 to C12 alkyl group, a linear or branched C1 to C12 alkylaryl group, an aryl group, or
$R_4$ and $R_5$ together form an optionally substituted ring system with at least 5 carbon atoms, and c) optionally one or more compounds selected from the group consisting of the general formulae (4) and (5)

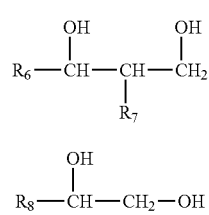

wherein
$R_6$ and $R_7$ are either both hydrogen or one is a methyl group and the other is hydrogen and $R_8$ is selected from the group consisting of a linear or branched C6 to C14 alkyl group, a linear or branched C6 to C14 alkyloxy group, a linear or branched C6 to C14 alkyloxyalkyl group, a linear or branched C6 to C14 alkylaryl, a linear or branched C6 to C14 alkylaryloxy and aryloxy group.

In the present invention a linear or branched C1 to C12 alkyl group include for example: a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3-dimethylhexyl group, a 4,4-dimethylhexyl group, a 5,5-dimethylhexyl group, a 1-propylpentyl group, a 2-propylpentyl group, an n-nonyl group, an n-decyl group, and n-dodecyl group etc. Those containing 1 to 8, preferably 1 to 6 carbon atoms, such as in particular methyl, ethyl, n-propyl, i-propyl, n-butyl, i-butyl, sec-butyl, and t-butyl, pentyl and the isomeric groups thereof, hexyl and the isomeric groups thereof, and octyl and the isomeric groups thereof, are preferred. C1-C3 alkyl, in particular, methyl, ethyl and i-propyl are more preferred. Most preferred are C1 and C2 alkyl, such as methyl and ethyl.

With respect to the linear or branched C1-C9 alkyl group it can be referred to the examples given for the linear or branched 01 to C12 alkyl group above.

With respect to the linear or branched divalent C2-C5 alkyl group for $R_2$ it can be referred to the examples given for the 01 to C12 alkyl group above, taking into account that there is an additional free valence forming the divalent alkyl group.

In the present invention an aryl group includes for example aromatic hydrocarbon residues containing 6 to 14 carbon atoms (excluding the carbon atoms of possible substituents), which may be monocyclic or bicyclic, including, for example: phenyl, naphthyl, phenanthrenyl and anthracenyl, particularly preferred is phenyl.

With respect to the 01 to C12 alkyl group in the linear or branched 01 to C12 alkylaryl group it can be referred to the examples given for alkyl above. With respect to the aryl group in the linear or branched 01 to C12 alkylaryl group it can be referred to the examples given for the aryl group above. Specific examples include e.g. tolyl, ethylphenyl etc.

A linear or branched 01 to C12 alkyloxy group, is a group C1-C12 alkyl-O— group, wherein alkyl is as defined before. With respect to the linear or branched C1-C9 alkyl group it can be referred to the examples given for the linear or branched 01 to C12 alkyl group above.

Examples of the C1 to C12 alkyloxy group include methoxy, ethoxy etc.

In the linear or branched C1 to C12 alkylaryloxy group, an aryl-O— group is substituted with one or more alkyl groups having 1 to 12 carbon atoms, such as the C1 to C12 alkyl group mentioned above. With respect to the aryl group it can be referred to the examples given above. Examples include e.g. tolyloxy, ethylphenoxy, etc.

An aryloxy group is an aryl-O— group wherein the aryl group is as defined above, such as phenoxy, etc.

With respect to the linear or branched C6 to C14 alkyl group, the linear or branched C6 to C14 alkyloxy group, the linear or branched C6 to C14 alkyloxyalkyl group, the linear or branched C6 to C14 alkylaryl, the linear or branched C6 to C14 alkylaryloxy and aryloxy groups for $R_8$. it can be referred to the above definitions for the corresponding C1-012 moieties taking into account that in addition C13 and C14 alkyl moieties are included such as the tetradecyl group, the tridecyl group or branched alkyl groups that have 13 or 14 carbon atoms such as 2,2,3-trimethyldecyl, 4,4-dipropylheptyl, 3-methyltridecyl, etc.

In accordance with the present invention an aqueous composition shall intend to mean any composition which contains water. Preferably the aqueous compositions according the invention comprises at least 10 wt-%, preferably at least 30 wt-%, more preferably at least 30 wt-% and still more preferably at least 40 wt-% water, and at most about 90 wt-% water, preferably at most about 80 wt-% water and more preferably at most 70 wt-% water, wherein the weight percentages relate to the total weight.

In a preferred embodiment of the accordance with the present invention, the aqueous compositions comprise in addition:
d) one or more substances selected from the group consisting of
i) nonionic surfactants,
ii) cationic surfactants,
iii) anionic surfactants,
iv) amphoteric surfactants,
v) oily phase-forming substance, preferably selected from saturated and unsaturated fatty oils and fats with between 8 and 32 carbon atoms,
vi) organic acids and polymeric derivatives thereof,
vii) polymeric thickeners,
viii) antioxidants, and
ix) pH adjusting agents.

In a preferred embodiment of the invention, the aqueous composition consists of the components a), b), c) and d).

In a particular preferred embodiment of the present invention the aqueous composition comprises at least one surfactant such as the surfactants i) to iv) mentioned above.

Preferably the aqueous compositions according to the invention, comprise the antimicrobial components a) and b) in a quantity producing a synergistic antimicrobial effect. These are in amounts, wherein the total weight of components a) and b) are reduced compared to the same weight of the individual components a) and b) to achieve essentially the same antimicrobial activity. It is surprising that the combination of the antimicrobial components a) and b) not only bring about an unexpected additive enhancement of the antimicrobial spectrum against microorganism, such as bacteria, yeasts, and particularly molds and fungi, but also gives rise to the synergistic effect, which potentiates the action of both components, in that the weight-percentages of the components required for their antimicrobial activity are distinctly reduced compared to the use of the same amount of the single components.

In a preferred embodiment according to the invention, the total weight of the sum of the components a), b) and optional c) in the aqueous composition is from 0.5 to 12 weight-%, preferably from 1.0 to 10 weight-%, more preferably from 1.5 to 7.5 weight-%, still more preferably from 1.5 to 5.0 weight-% based on the total weight of the aqueous composition. Still more preferred the total weight of the sum of the components a) and b) in the aqueous composition is from 0.5 to 10 weight-%, preferably from 1.0 to 7.5 weight-%, more preferably from 1.5 to 5.0 weight-%, based on the total weight of the aqueous composition.

In a further preferred embodiment of the invention, the aqueous composition comprises 0.4 to 2.0 weight-% of the total of the components a), and 0.1 to 5.0 weight-% of the total of components b).

In another preferred embodiment of the invention the aqueous composition comprises 0.4 to 2.0 weight-% of the total of components a), 0.1 to 5.0 weight-% of the total of components b) and 0.1 to 5.0 weight-% of the total of components c), and wherein the sum of the total of components b) and c) is from 0.2 to 6.0 weight-%), each percentage being based on the total weight of the aqueous composition.

In a further preferred embodiment according to the invention, the amount of the one or more silicones in the aqueous composition is in the range of 1 and 50 weight-%, preferably between 5 and 40 weight-%, and more preferably between 10 and 30 weight-% based on the total weight of the aqueous composition.

In a further preferred embodiment according to the invention, the aqueous composition is in the form of an emulsion, preferably selected from a microemulsion or an oil-in-water emulsion. In the present invention, a microemulsion shall include in particular an emulsion wherein the disperse oil phase has a particle size sufficiently small (typically less than 100 nm in diameter) that visible light is essentially not scattered and the emulsion appears transparent.

In a further preferred embodiment according to the invention, the aqueous composition is free of parabens.

In the aqueous compositions according to the invention the silicones are preferably selected from the group consisting of polyorganosiloxanes which optionally may have one or more functional groups, preferably said silicones are selected from polydimethylsiloxanes, amino group-modified silicones, polyether group-modified silicones, and silicones comprising at least one quaternary ammonium group and mixtures thereof. Particular preferred are amino group-modified silicones and/or silicones comprising at least one quaternary ammonium group (so called "quats"). In another preferred embodiment, the aqueous composition according to the invention comprises at least one silicone which is selected from linear or branched polydimethylsiloxanes with a viscosity equal to or greater than 350 mPa*s at 25° C. determined according to DIN 53015: Viscometry—Measurement of viscosity by means of the rolling ball viscometer by Höppier.

In a particular preferred embodiment the aqueous composition according to the invention comprises at least one amino group-modified silicone selected from the group consisting of linear or branched polydimethylsiloxanes having at least one aminoalkyl group, preferably selected from the group consisting of terminal and pendant aminopropyl and/or aminoethylaminopropyl groups, having preferably 0.1 to 0.9 mmol/g amino functionality.

In particular preferred embodiment the aqueous composition according to the invention comprises at least one silicone which is selected from the group consisting of a silicone comprising at least one quaternary ammonium group, preferably selected from the group consisting of silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-17, silicone quaternium-18, silicone quaternium-20, silicone quaternium-21, silicone quaternium-22, silicone quaternium-25, and silicone quaternium-26, and mixtures thereof.

Preferred structures of quaternized silicone polymers which can be used in the aqueous composition according to the invention are disclosed i.e. in WO2016046178, US2006235181, US2006223939, WO2009115412, WO2009042083, US2009076238, U.S. Pat. Nos. 7,041,767, 7,217,777, WO2011147959, US2008213208, WO2013148629, WO2013148935, WO2013148635, WO2004069137, US2011033411, US2011182844, US, 2010044615, US2010210809, US2011039948, US2005255073, US2007106045, WO2009042083. The references regarding quaternized silicone polymers cited in these prior art disclosures are incorporated herewith explicitly.

Preferably the silicones are selected from the list consisting of polydimethylsiloxanes, aminosilicones, silicone copolyols, quaternized silicones or quaternized silicone copolyols.

Preferred silicone polymers for cosmetic compositions are polydimethylsiloxanes, aminosilicones and quaternized silicones. Preferred is also a linear or branched polydimethylsiloxane with a viscosity of at least 5 mPa*s at 25° C., preferably greater than 100 mPa*s at 25° C., more preferably with a viscosity of greater than 350 mPa*s at 25° C., and most preferably with a viscosity of greater than 100,000 mPa*s at 25° C. (viscosities being determined according to DIN 53015: Viscometry—Measurement of viscosity by means of the rolling ball viscometer by Höppler). The polydimethylsiloxane can be incorporated into the composition as such, or formed by emulsion polymerization of either a cyclic polydimethylsiloxane or a short chain polydimethylsiloxanediol.

Further the aminosilicone can be any polydimethylsiloxane with either terminal or pendant aminoalkyl functional groups bonded to silicone by a carbon atom. Preferably the aminosilicone is a polydimethylsiloxane with either terminal or pendant aminopropyl or aminoethylaminopropyl functional groups and with 0.1 to 0.9 mmol/g amino functionality. The silicone copolyols include any copolymers of polydimethylsiloxanes and polymeric polyols formed by polymerization of ethylene oxide and/or propylene oxide, wherein the polyol is bound to the siloxane in either a terminal or pendant position by either a silicone-to-carbon or silicone-to-oxygen bond.

The quaternized silicone polymer include any polydimethylsiloxane polymer with one or more quaternary ammonium groups either in the polymer chain or attached in a pendant position by an organic linkage group. Preferred are quaternized silicone polymers described according to the International Nomenclature of Cosmetic Ingredients (INCI) as quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-17, silicone quaternium-18, silicone quaternium-20, silicone quaternium-21, silicone quaternium-22, silicone quaternium-25, and silicone quaternium-26. Also the quaternized silicone polymers such as silicone quaternium-2-panthenol succinate and silicone quaternium-16/glycidal dimethicone cross polymer are included. Especially preferred are the quaternized silicone polymers silicone quaternium-15, silicone quaternium-16, silicone quaternium-18, silicone quaternium-22, silicone quaternium-25 and silicone quaternium-26. The quaternized silicone copolyols are quaternized silicone polymers that in addition contain at least one polyol attached in a pendant position by an organic linkage group.

The aqueous composition according to the invention preferably comprises 0.1 to 5.0 weight-%, preferably 0.1 to 3.0 weight-%, more preferably 0.1 to 2.0 weight-% of the total amount of the components a) based on the total weight of the aqueous composition.

In a preferred embodiment of the aqueous composition according to the invention the component a) is selected from the group consisting of 2-phenoxyethanol, 2-phenylethanol or 3-phenylpropanol and a derivative thereof, wherein in said derivative $R_1$ is a C1-C9 alkyl group or a methoxy group and $R_1^*$ and $R_1^{**}$ are each hydrogen, and mixtures thereof. Most preferably component a) is 2-phenoxyethanol and/or 3-phenyl-1-propanol:

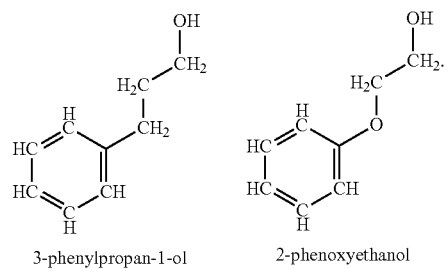 [SMILES: OCCCc1ccccc1 ; OCCOc1ccccc1]

3-phenylpropan-1-ol     2-phenoxyethanol

In a preferred embodiment of the invention the aqueous composition comprises 0.1 to 5.0 weight-%, preferably 0.1 to 3.0 weight-%, more preferably 0.1 to 2.0 weight-% of the total weight of the components b) based on the total weight of the aqueous composition. Preferably the component b) is selected from the group consisting of 2-methyl-2,4-pentanediol, 2-methyl-2,4-hexanediol, 2,2-dimethyl-1,3-propanediol, 2-methyl-2-propyl-1,3-propanediol, 2,2-dibutyl-1,3-propanediol, 2-butyl-2-ethyl-1,3-propanediol and 2,2-dioctyl-1,3-propanediol, and mixtures thereof, preferably component b) is selected from 2-butyl-2-ethyl-1,3-propanediol (BEPD), 2-methyl-2,4-hexanediol (HG), and 2-methyl-2-propyl-1,3-propanediol (MPPD):

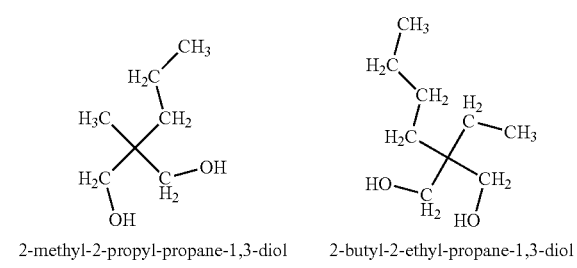

2-methyl-2-propyl-propane-1,3-diol     2-butyl-2-ethyl-propane-1,3-diol

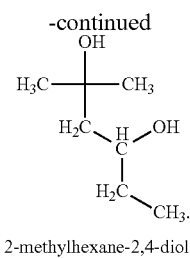

2-methylhexane-2,4-diol

Component c) is an optional compound of formulae (4) and (5) as defined above. In case the optional component c) is present in the aqueous composition, preferably the aqueous composition comprises 0.1 to 5.0 weight-%, preferably 0.1 to 3.0 weight-%, more preferably 0.1 to 2.0 weight-% of the total weight of the components c) based on the total weight of the aqueous composition.

Preferably component c) is selected from the group consisting of 1,2-octanediol, 1,2-decanediol, 3-(2-ethylhexyloxy)-1,2-propanediol, 1,2-dodecanediol, 1,2-octanediol, 2-methyl-1,3-propanediol, 1,3-propanediol and 1,3-butanediol, and mixtures thereof, preferably component c) is selected from 3-(2-ethylhexyloxy)-1,2-propanediol (or ethylhexylglycerin (EHG):

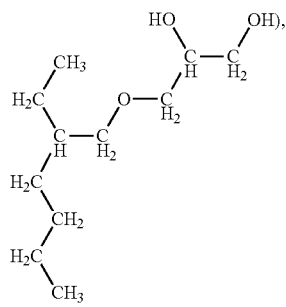

1,3-propanediol (PD), 1,2-dodecanediol (DD), 1,2-octanediol (OD) and 2-methyl-1,3-propanediol (MPD).

The present invention also relates to the use of the aqueous composition according to the invention for the manufacture of an article selected from group of home care articles, personal care articles, household articles, industrial articles, fabric articles, cosmetic articles, hygienic articles, and medical articles. Non-limiting embodiments of household and industrial articles include for example householder cleaners such as concentrated liquid cleaners and spray cleaners, cleaning wipes, dish washing liquid, dish washer detergent, spray-mop liquid, furniture polish, indoor paint, outdoor paint, dusting spray, laundry detergent, fabric softener, rug/fabric cleaner, window and glass cleaner, toilet bowl cleaner, liquid cream cleanser, car cleaners, car polish, floor cleaner, etc. Home care or personal care products include in particular cosmetic products such hair care products such as hairsprays, shampoos, mousses, styling gels and lotions, cream rinses/conditioners, hair tonics, hair dyes and colorants, home permanents and bleaches etc., which are specified in more detail below. Also included are skin care products such as cleansers, conditioners, lipsticks, eye makeup, fingernail polish, suntan products, antiperspirant/deodorant products and depilatories etc., which are specified in more detail below. Also included are household products such as waxes, polishes, heavy and light duty liquids, fabric softeners and window cleaners. Also included are fabric treatment articles and the treated fabric articles, such as detergents, laundry detergents, fabric treatment compositions, such as fabric finishing compositions etc. Also included are hygienic and medical articles such disinfectant compositions etc., as described in more detail below.

Cosmetic products may include in particular "decorative" and "care" cosmetics. The cosmetics can be liquid or cream emulsions; powders, both pressed and loose; dispersions; and anhydrous creams or sticks etc. Cosmetic products that can be applied to the face such as skin-care creams, lipsticks, eye and facial makeup, towelettes, and colored contact lenses. Cosmetic products that can be applied to the body such as deodorants, lotions, powders, perfumes, baby products, bath oils, bubble baths, bath salts, and body butters; to the hands/nails: fingernail and toe nail polish, and hand sanitizer; to the hair: permanent chemicals, hair colors, hair sprays, and gels; makeup compositions comprising color pigments, cosmetic products that can applied in particular to the face and eye area such as primers, foundations or eyeshadows, lipsticks, lip gloss, lip liner, lip plumper, lip balm, lip stain, lip conditioner, lip primer, lip boosters, and lip butters which may contain sunscreens, concealers, face powders, mascara, eye shadow, eye liner, eyebrow pencils, creams, waxes, gels, and powders which are used to color, fill in, and define the brows; lotions, cleansing formulations; toners; facial masks; peel masks, sheet masks, exfoliant products, moisturizers such as creams or lotions which may contain essential oils, herbal extracts, or other chemicals; night creams, day creams, sunscreen compositions, nail polishes etc. The aqueous compositions according to the invention can be (used in or) formulated into a form typical for hair treatment compositions. Preferred are topical hair care or treatment compositions, e.g. hair tonics, conditioners, hair-care preparations, e.g. pre-treatment preparations, styling creams, styling gels, pomades, hair rinses, treatment packs, intensive hair treatments e. g. leave-on and rinse-off deep conditioners, hair-structuring preparations, e.g. hair-waving preparations for permanent waves (hot wave, mild wave, cold wave), hair-straightening preparations, liquid hair-setting preparations, hair foams, hair serums, hair sprays, bleaching preparations, e g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile. Based on the application the hair care preparations may be in particular in the form of a (aerosol) spray, (aerosol) foam, gel, gel spray, cream, lotion, liquid, serum or a wax, mousse, shampoo, such as pearl shampoo, anti-frizz shampoo etc. The aqueous compositions according to the invention can be used as leave-on or rinse-off hair treatment compositions.

Personal care articles, including the cosmetic and medical articles, which may comprise the aqueous compositions according to the invention include e.g. bar soap, liquid soap (e.g., hand soap), hand sanitizer (including rinse off and leave-on alcohol based and aqueous-based hand disinfectants), preoperative skin disinfectant, cleansing wipes, disinfecting wipes, body wash, acne treatment products, skin cream, shampoo, conditioner, cosmetics (including but not limited to liquid or powder foundation, liquid or solid eyeliner, mascara, cream eye shadow, tinted powder, "pancake" type powder to be used dry or moistened, etc.) deodorant, antimicrobial creams, body lotion, hand cream, topical cream, aftershave lotion, skin toner, mouth wash, toothpaste, sunscreen lotion, and baby products such as, but not limited to, cleansing wipes, baby shampoo, baby soap, and diaper cream, Wound care items, such as, but not limited to, wound healing ointments, creams, and lotions, wound coverings, burn wound cream, bandages, tape, and steri-strips, and medical articles such as medical gowns, caps, face masks, and shoe-covers, surgical drops, etc. Additional products include but are not limited to oral products such as mouth rinse, toothpaste, and dental floss coatings, veterinary and pet care products, preservative compositions, and surface disinfectants including solutions, sprays or wipes, etc.

The invention also relates to a process for the preparation of the aqueous compositions according to the invention, comprising the steps of:
(a) mixing one or more of the components a) and b) and optionally one or more component c),
(b) adding the one or more silicones as defined above,
(c) then adding water, and
(d) optionally adding at least one or more components d) in one or more additional process steps to prepare the aqueous composition. More preferred embodiments of such process are described below.

The invention also relates to articles comprising at least one aqueous composition according to the invention, selected from the home care articles, household articles, industrial articles, fabric articles, cosmetic articles, hygienic articles, and medical articles as described above. Said articles may comprise preferably 0.01 to 30 weight-%, preferably 0.1 to 25 weight-% of one or more silicones and 0.01 to 10 weight-% of the total of the components a), b) and optionally c), based on the total weight of the article. More preferably the articles according to the invention comprise 0.5 to 10 weight-% of one or more silicone polymers and 0.2 to 5 weight-% of the total of the components a), b) and optionally c). The articles according to the invention in addition to the aqueous compositions according to the invention preferably comprise one or more functional components e), which are preferably selected from the group consisting of:
i) volatile silicone compounds different from the silicones comprised in the aqueous compositions according to the invention,
ii) anionic, nonionic, cationic or amphoteric surfactants,
iii) oily phase-forming substance, preferably selected from saturated and unsaturated fatty oils and fats with between 8 and 32 carbon atoms,
iv) saturated and unsaturated aliphatic alcohols, different from components a), b) and c) as defined above,
v) organic acids and polymeric derivatives thereof,
vi) antioxidants,
vii) UV absorbers,
viii) perfumes and fragrances,
ix) dyes and pigments,
x) hydrophilic components or polymers,
xi) emollients,
xii) organic polymeric quaternary ammonium compounds,
xiii) antidandruff agents,
xiv) antiperspirants,
xv) insect repellants,
xvi) vitamins or vitamin precursors,
xvii) botanical extracts,
xviii) inorganic or polymeric thickeners,
xix) additional components with antimicrobiological properties, preferably selected from the group consisting of short chain alcohols different from components a), b) and c) as defined above,
xx) silicone and organic polymer fixatives, and
xxi) organic solvents.

Preferably the articles according to the invention consist of the aqueous compositions of the invention as defined above and one or more of the functional components e).

The articles according to invention preferably are in the form of an oil-in-water emulsion, a dispersion, a microemulsion, or a water-in-oil cream.

The present invention also relates to a method for the cosmetic, hygienic, medical or cleansing treatment, which comprises the application of the articles according to the invention to at least one substrate, preferably selected from skin, hair, household goods and industrial goods, where the silicones exert in particular their surface functionality.

The present invention also relates to a method of preserving aqueous compositions comprising at least one silicone by adding a mixture of components a) and b), and optionally component c), as defined above, and the use of a mixture of components a) and b), and optionally component c), as defined above for preserving aqueous compositions comprising at least one silicone against microorganism, such as bacteria, yeasts, and particularly molds and fungi. The present invention also relates to a preservative composition comprising a mixture of components a) and b) and optionally component c) as defined above.

Accordingly the present invention provides aqueous compositions of silicone polymers that are stable against microbiological growth caused by bacteria, yeasts, and in particular molds or fungi. Surprisingly, it was found that in accordance with the invention the substituted 1,3-propanediols b) synergistically enhance the antimicrobial activity of aromatic alcohols a), and thereby allow for a more effective microbiological control of the aqueous compositions comprising one or more silicones. In particular, if the aromatic alcohols are used at the level of less than or equal to 1.0 wt-%, alone they would not provide adequate antimicrobiological properties, in particular against certain molds or fungi, whereas the inventive aqueous compositions comprising the aromatic alcohols a) and the substituted 1,3-propanediols b) provide adequate control of microbiological growth even when the compositions are inoculated with significant concentrations of live organisms.

The inventive components a), b) and optionally c) are in some cases of low water solubility, accordingly in another embodiment of the present invention a process is provided for preparation of the inventive aqueous compositions. According to the inventive process one or more of the components a), b) and optional c) are first mixed alone or together with the silicone polymer then combined with water and the additional components d) in one or more additional process steps to prepare the final microbiologically stable aqueous composition according to the state-of-the-art for such compositions. It is preferred to use agitation in the inventive process of mixing the one or more silicone polymers with the components a), b) and optional c). It is also preferred to apply heat during agitation, in particular if one or more of the components a) b) or c) is a solid or wax at ambient temperature. After the mixture of the one or more silicone polymers with the components a), b) and c) is homogeneous, then the additional components d) and water can be added in any particular order. It was found that the inventive process provides for particularly good antimicrobiological properties, at particularly low levels of the inventive components a), b) and c), as compared to other processes wherein the aqueous emulsion or microemulsion of the siloxane polymer is first prepared and then the components a, b) and c) are added subsequently.

As is well-known to a skilled person in the art the exact level of components a), b) and optionally c) required for microbiological stability is dependent for example upon the kind of silicone polymer, and its content, the concentration of the one or more components d) as well as the pH of the composition. It is also well-known that some of the components d) can influence the microbiological properties of the composition. For example, several of the components d), including but not limited to cationic surfactants, organic acids and polymeric derivatives thereof, and antioxidants, are known to also exhibit antimicrobiological properties, whereby the amount of the components a), b) and c) required for microbiological stability can be reduced.

The inventive aqueous composition of one or more silicone polymers can have a pH value of between 3 and 10, preferably between 6 and 9 (at room temperature). The pH value of the composition can be an inherent result of the composition comprising the silicone polymer and the components a), b), c) and d) i)-viii) as defined above, or it can be achieved by adjustment of the pH with the components d) ix) as defined above. Most preferably the pH of the composition is adjusted to a neutral pH of between 6 and 8.

Also preferred are cosmetic, hygienic, medical or household cleansing articles comprising the inventive composition of one or more silicone polymers, wherein the articles comprise or consist of, in addition to the components a) b) and optionally c), d) and e), also additional components with microbiological properties taken from the list consisting of parabens, isothiazolinones and 3-iodo-2-propinylbutylcarbamate. It is most preferred to use these additional components with microbiological properties at low levels. Especially preferred is to use less than 2.0%, most preferred to use less than 1.0%, of a combination of these components. In a preferred embodiment according to the invention, the articles do not contain parabens.

Also preferred are cosmetic, hygienic, medical or household cleansing articles comprising the inventive composition of one or more silicone polymers, wherein the articles comprise in addition to the components a), b) and optionally c), d) and e) also antimicrobiologically active organic acids, such as benzoic acid, sorbic acid, dehydroacetic acid and salicylic acid, and their respective salts, and preferably the pH of the article is adjusted to a value of 5 or below. Also preferred are cosmetic, hygienic, medical or household cleansing articles comprising the inventive composition of one or more silicone polymers, wherein the articles comprise in addition to the components a), b) and optionally c), d) and e) also antimicrobiologically active fragrance components as described in European Patents Nos. 1543829 and 1543830 or the botanical extracts as described in WO Patent No. 2011/002929.

Also preferred are cosmetic, hygienic, medical or household cleansing articles comprising the inventive composition of one or more silicone polymers, wherein the articles comprise in addition to the components a), b) and optionally c), d) and e) also antioxidants such as 3(2)-tert-butyl-4-methoxyphenol, 2,6-di-tert-butyl-4-methylphenol, tocopherol and vitamin E. In still another preferred embodiment of the present invention, a process for preparing cosmetic, hygienic, medical or household cleansing article is provided whereby the components a), b) and or c) are first mixed alone or together with the one or more silicone polymer then combined with water and the additional components d) and e) before conversion to the final cosmetic, hygienic, medical or household cleansing articles according to the state-of-the-art for such articles.

In the following, the preferred embodiments of the silicones and the components a) to e) used in the aqueous compositions of the invention are summarized. In the present invention components d) and e) are understood to be different from the one or more silicones and components a) to c) as the mandatory components of the aqueous composition according of the invention.

The aromatic alcohol corresponding to component a) includes any alcohol of general formula (1) as defined above, and examples thereof include 2-phenoxyethanol, 3-phenyl-1-propanol, 2-phenylethanol, 4-phenyl-1-butanol, 3-phenyl-1-butanol, 2-phenyl-1-butanol, 2-methyl-1-phenyl-2-propanol and the aryl-substituted derivatives thereof. Benzyl alcohol and substituted benzyl alcohols are excluded. Examples of inventive aryl substituted derivatives include 2-(4-methyphenoxy)ethanol, 2-(4-methylphenyl)ethanol, 2-(3-methylphenyl)ethanol, 2-(2-methylphenyl)ethanol, 2-(2-methoxyphenyl)ethanol, 2-(2-methoxyphenyl)ethanol, 2-(3-methoxyphenyl)ethanol, 2-(4-methoxyphenyl)ethanol, 3-(4-methoxyphenoxy)-1-propanol, 3-(2-methoxyphenyl)-1-propanol, 3-(3-methoxyphenyl)-1-propanol, 3-(4-methoxyphenyl)-1-propanol. Preferred are 2-phenoxyethanol, 2-phenylethanol or 3-phenyl-1-propanol or a derivative thereof wherein in particular $R_1$ a C1-C9 alkyl substituent or a methoxy group and $R_1^*$ and $R_1^{**}$ are hydrogen.

The substituted 1,3-propanediol corresponding to component b) includes any compound selected from the group consisting of the general formulae (2) and (3) as defined above, and examples of the substituted 1,3-propanediols include 2-methyl-2,4-pentanediol, 2,2-dimethyl-1,3-propanediol, 2-methyl-2-ethyl-1,3-propanediol, 2-methyl-2-propyl-1,3-propanediol, 2-methyl-2-butyl-1,3-propanediol, 2,2-diethyl-1,3-propanediol, 2,2-dibutyl-1,3-propanediol, 2-butyl-2-ethyl-1,3-propanediol, 2-methyl-2-phenyl-1,3-propanediol, 2,2-dioctyl-1,3-propanediol, 2,2-didecyl-1-3-propanediol, 2-cyclohexyl-2-methyl-1,3-propanediol, 2-pentyl-2-propyl-1,3-propanediol, 2-(2-methylbutyl)-2-propyl-1,3-propanediol, 2-benzyl-2-methyl-1,3-propanediol, 2-octyl-2-methyl-1,3-propanediol, 2-isopropyl-2-methyl-1,3-propanediol, 1,1-dimethylolcyclopentane, 1,1-dimethylolcyclohexane, and 1,1-dimethylolcyclooctane. Preferred are 2,2-dimethyl-1,3-propanediol, 2-methyl-2-propyl-1,3-propanediol, 2,2-dibutyl-1,3-propanediol, 2-butyl-2-ethyl-1,3-propanediol, and 2,2-dioctyl-1,3-propanediol. Especially preferred is 2-methyl-2,4-pentanediol.

The Alkanediol of the General Formula (4) Corresponding to Component c):

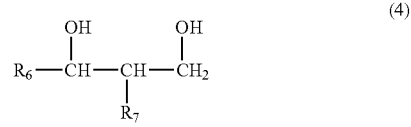

(4)

includes any 1,3-alkanediol with 3 to 5 carbon atoms, and examples are 1,3-propanediol, 2-methyl-1,3-propanediol and 1,3-butanediol.

The Alkanediol of the General Formula (5) Corresponding to Component c):

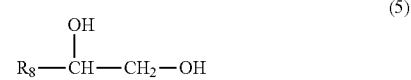

(5)

includes any alkanediol wherein $R_8$ is a linear or branched C6 to C14 alkyl, alkyloxy, alkylaryl, alkylaryloxy or aryloxy group and examples of the 1,2-alkanediols include: 1,2-octanediol, 1,2-nonanediol, 1,2-decanediol, 1,2-undecanediol, 1,2-dodecanediol, 1,2-octadecanediol, 3-(2-ethylhexyloxy)-1,2-propanediol (also known as ethylhexyl glycerin), 3-(2-hydroxydodecyloxy)-1,2-propanediol, 3-(2-hydroxydecyloxy)-1,2-propanediol, 3-octyl-1,2-propanediol, 3-decyl-1,2-propanediol, 3-dodecyl-1,2-propanediol, 3-phenyl-1,2-propanediol, 3-phenoxy-1,2-propanediol, 3-(4-methylphenoxy)-1,2-propanediol and 3-(4-methoxyphenoxy)-1,2-propanediol. Preferred are 1,2-octanediol, 1,2-decanediol, 3-(2-ethylhexyloxy)-1,2-propanediol and 1,2-dodecanediol.

The nonionic surfactants d) i) or e) ii) include, but are not limited to: alkyl glucosides, alkyl polyglucosides, polyhydroxy fatty acid amides, sucrose esters, esters of fatty acids and polyhydric alcohols, fatty acid alkanolamides, ethoxylated and/or propoxylated, saturated and unsaturated fatty acids, ethoxylated and/or propoxylated, saturated and unsaturated aliphatic acids, ethoxylated and/or propoxylated, saturated and unsaturated fatty alcohols, ethoxylated and/or propoxylated saturated and unsaturated aliphatic synthetic alcohols, ethoxylated and/or propoxylated glycerides, block copolymers of ethylene oxide and propylene oxide (such as the Pluronic and Tetronic surfactants available from BASF), ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, and ethoxylated polyoxypropylenes. In certain preferred embodiments, the nonionic surfactants useful in the compositions of the present invention are selected from the group consisting of alkyl polyglucosides, ethoxylated, saturated and unsaturated fatty acids, ethoxylated aliphatic acids, ethoxylated, saturated and unsaturated fatty alcohols and ethoxylated aliphatic synthetic alcohols.

The cationic surfactants d) ii) or e) ii) include any organic surfactant with a positively charged group. Examples of the inventive cationic surfactants are the salts of tetraalkylammonium, trialkylarylammonium, trialkylbenzylammonium, alkylamidoalkyltrialkylammonium, trialkylhydroxyalkylammonium, alkylpyridinium cations with anionic counterions. The inventive salts include counterions such has halides (preferably chlorides or bromides) or alkyl sulfates such as methosulfate or ethosulfate. Examples of the cationic surfactants also include imidazoline derivatives and amine oxides. Examples of the cationic surfactants include benzyltrimethylammonium chloride, laurylbenzyldimethylammonium chloride, hexadecyltrimethylammonium chloride, oleoyltrimethylammonium chloride, didecyldimethylammonium chloride, dicocodimethylammonium chloride, cocobenzyldimethylammonium chloride, alkylpyridinium halides, lauryldimethylamine oxide, laurylamidopropyldimethylamine oxide, cocodimethylamine oxide, stearylamine oxide and cetyl amine oxide The anionic surfactants d) iii) or e) ii) include any surfactant with an alkyl, alkylaryl or aryl group and a carboxylate, sulfate, sulfonate or phosphonate group that is optionally ethoxylated. Examples include, but are not limited to, linear and branched fatty acids salts, sarcosinates, taurides, isethionates, glutamates, alkyl sulfonates, alkyl sulfates, alkyl ether sulfates, sodium or potassium alkyl sulfates, ammonium alkyl sulfates, sodium, potassium or ammoninium salts of taurides, sarcosides, or isethionates, alkyl and alkylaryl glycerylether sulfonates, alkyl, dialkyl, alkylaryl and dialkylaryl sulfosuccinates, N-alkyl sulfosuccinamates, alkylglyceryl ether sulfonates, alkyl phosphates, alkyl ether phosphonates, alkylaryl phosphates, alkyl phosphonates, and alkylaryl phosphonates. These anionic surfactants may have an alkali or alkaline metal or organic ammonium counterion. Preferred are sodium, potassium or ammonium salts of alkyl sulfonates, alkyl sulfates, alkyl ether sulfates, isethionates and sarcosides.

The amphoteric surfactants d) iv) or e) ii) include any organic surfactant that has both acidic and basic groups, often referred to as zwitterions or zwitterionic compounds. The surfactants include those having tertiary amine groups, which may be protonated, as well as quaternary amine containing zwitterionic surfactants. Examples of useful amphoteric surfactants include ammonium carboxylate amphoterics and ammonium sulfonate amphoterics. Examples of such amphoteric surfactants include, but are not limited to, betaines, such as cocobetaine and cocoamidopropyl betaine, monoacetates such as sodium lauroamphoacetate; diacetates such as disodium lauroamphoacetate; amino- and alkylamino-propionates such as lauraminopropionic acid, cocamidopropylhydroxysultaine. Preferred are alkylamidopropyl betaines, in particular cocoamidopropyl betaine.

The volatile silicones e) i) include all low molecular weight silicones with a significant vapor pressure at 25° C. Examples of the volatile silicones include cyclic polydimethylsiloxanes, such as octamethylcyclotetrasiloxane, decamethylcyclopentasiloxane, dodecamethylcyclohexasiloxane, hexamethyldisiloxane, octamethyltrisiloxane, 2-ethyl-heptamethyltrisiloxane and 2-propyl-heptamethyltrisiloxane. Preferred are the cyclic siloxanes decamethylcyclopentasiloxane and dodecamethylcyclohexasiloxane The oily phase-forming substance d) v) or e) iii) include any animal and/or plant oils and fats with preferably between 8 and 32 carbon atoms. Examples include, but are not limited to: olive oil, sunflower oil, refined soya oil, palm oil, sesame oil, rapeseed oil, argan oil, ricinus seed oil, wheat germ oil, almond oil, borage oil, evening primrose oil, coconut oil, shea butter, jojoba oil, sperm oil, beef tallow, cacao butter, mango butter, neat's foot oil and lard and any of the fatty acids, their respective esters having 8 to 32 carbon atoms as well as the alcohols derived from these oils. Non-limiting examples include: lauric acid and esters, lauryl alcohol, myristic acid and esters such as isopropylmyristate, myristyl alcohol, palmitic acid and esters such as 2-ethylhexylpalmitate and isopropylpalmitate, cetyl alcohol, oleic acid and esters such as cetyloleate and oleyloleate, oleyl alcohol, linoleic acid and esters, stearic acid and esters such as 2-ethylhexylstearate, stearyl alcohol, erucic acid and esters behenyl alcohol, and the like. The esters include as non-limiting examples the methyl, ethyl, isopropyl, and trimethylolpropane esters and the like.

The saturated or unsaturated aliphatic alcohol e) iv) are different from components a), b) and c) as defined above, and preferably have in total between 8 and 22 carbon atoms including any linear or branched aliphatic primary or secondary alcohol including naturally occurring primary alcohols or mixtures thereof. Examples of such aliphatic alcohols are 1-octanol, 1-decanol, 2-decanol, 1-undecanol, 2-undecanol, 10-undecen-1-ol, 1-dodecanol, 2-dodecanol, 2-butyl-1-octanol, 2-ethylhexan-1-ol, 3,5,5-trimethylhexan-1-ol, cis-8-octadecen-1-ol, lauryl alcohol, myristyl alcohol, cetyl alcohol, oleyl alcohol, stearyl alcohol, behenyl alcohol and 1-octadecanol. Preferred are 1-decanol, 1-undecanol, 10-undecen-1-ol, 1-dodecanol, cis-8-octadecen-1-ol and 1-octadecanol and mixtures thereof.

The organic acids e) v) or d) vi) include any saturated or unsaturated aliphatic or aromatic carboxylic acid including fatty acids. Examples of the organic acids are citric acid, glycolic acid, lactic acid, malic acid, tartaric acid, acetic acid, lauryl acid, caprylic acid, 2-ethylhexanoic acid, cis-9-octadecenoic acid, oleic acid, stearic acid, isostearic aicd, palmatinic aicd, isopalmitinic acid, benzoic acid, 4-hydroxybenzoic acid, 2,4-hexadienoic acid, sorbic acid, dehydroacetic acid and salicylic acid. Preferred are the fatty acid mixtures derived from coconut oil and palm oil. The organic acids can be used in the form of their alkali, alkaline or other metal or ammonium salts, for example sodium benzoate, potassium sorbate, or sodium salicylate. Many of these organic acids are known to have antimicrobiological properties, at pH values of below 6. Preferred are the organic acids such as benzoic acid, sorbic acid, dehydroacetic acid and salicylic acid and their respective salts.

The polymeric derivatives of the organic acids e) v) or d) vi) include any organic polymers with free carboxylic, phosphonic or sulfonic acid groups. Examples of polymeric organic acids include naturally occurring carboxylic acid functional polymers such as hyaluronic acid and derivatives of natural polymers such as carboxymethylcellulose, alginic acid and other alginate polymers, Fucogel (a polysaccharide consisting of three mono-saccharides, fucose, galactose, and galacturonic acid), hyaluronic acid, and the like. Examples of synthetic polymeric acids include those based upon carboxylic acid, phosphonic acid, or sulfonic acid functional monomers, including but not limited to, polymers and copolymers derived from acrylic acid, methacrylic acid, maleic anhydride, itaconic anhydride, sodium AMPS (the sodium salt of 2-acrylamido-2-methylpropane sulfonic acid), sulfopropyl acrylate or methacrylate, sulphomethylated acrylamide, allyl sulphonate, sodium vinyl sulphonate, combinations thereof.

The antioxidants e) vi) include all compounds that reduce the rate of oxidation of organic components in the composition. Non-limiting examples of inventive antioxidants are phenolic compounds such as butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, 4-hydroxybenzoic acid methyl ester, dodecyl gallate, pyrogallate, and tocopherol or vitamin E. Preferred are 3(2)-tert-butyl-4-methoxyphenol, 2,6-di-tert-butyl-4-methylphenol and tocopherol.

The UV-absorbers e) vii) include any compounds commonly used in cosmetic formulations and skin creams to filter UV-irradiation from sunlight, including but not limited to derivatives of benzoic acid and esters thereof, cinnamic acid and esters thereof, salicylic acid and esters thereof, and compounds of the oxanilide type, triazine type, triazole type, vinylamide type, cinnamide type, aminophenylthiazole type, benzophenone type or merocyanine type. Examples are aminobenzoic acid, p-aminobenzoic acid ethyl ester ethoxylated, p-dimethylaminobenzoic acid-2-ethylhexyl ester, p-aminobenzoic acid ethyl ester (2 mol) N-propoxylated-p-aminobenzoic acid glycerol ester, salicylic acid homomenthyl ester, salicylic acid-2-ethylhexyl ester, triethanolamine salicylate, 4-isopropyl benzyl salicylate—anthranilic acid menthyl ester, diisopropyl cinnamic acid ethyl ester, p-methoxycinnamic acid-2-ethylhexyl ester, diisopropyl cinnamic acid methyl ester, p-methoxycinnamic acid isoamyl ester, p-methoxycinnamic acid diethanolamine salt, p-methoxycinnamic acid isopropyl ester, 2-ethylhexyl-2-cyano-3,3-diphenyl acrylate, ethyl-2-cyano-3,3'-diphenyl acrylate-2-phenylbenzimidazole sulfonic acid and salts, 3-(4'-trimethylammonium) benzylidene bornan-2-one methyl sulfate, terephthalylidene dibornane sulfonic acid and salts, 4-t-butyl-4'-methoxydibenzoyl methane (avobenzone), urocanic acid, 2-hydroxy-4-methoxybenzophenone, 2-hydroxy-4-methoxybenzophenone-5-sulfonic acid, dihydroxy-4-methoxybenzophenone, 2,4-dihydroxybenzophenone, tetrahydroxybenzophenone, 2,2'-dihydroxy-4,4'-dimethoxybenzophenone, 2-hydroxy-4-n-octoxybenzophenone, 2-hydroxy-4-methoxy-4'-methyl benzophenone, 3-(4'-sulfo)benzylidene bornan-2-one and salts, ubichinone, 3-(4'-methyl benzylidene)-d,l-camphor, 3-benzylidene-d,l-camphor, 4-isopropyl dibenzoyl methane, 2,4,6-trianilino-(p-carbo-2'-ethylhexyl-1'-oxy)-1,3,5-triazine, phenylene bis-benzimidazyl tetrasulfonic acid disodium salt, 2,2'-(1,4-phenylene)-bis-(1H-benzimidazole-4,6-disulfonic acid), monosodium salt, N-[(2 and 4)-[2-(oxoborn-3-ylidene) methyl]benzyl] acrylamide polymer, phenol, -(2H-benzotriazol-2-yl)-4-methyl-6-(2-methyl-3(1,3,3,3-tetramethyl-1-(trimethylsilyl)oxy)disiloxyanyl)propyl), 4,4'-[(6-[4-(1,1-dimethyl)aminocarbonyl) phenylamino]-1,3,5-triazine-2,4-diyl)diimino]-bis-(benzoic acid-2-ethylhexyl ester), 2,2'-methylene bis-(6-(2H-benzotriazol-2-yl)-4-1,1,3,3-tetramethylbutyl) phenol), 2,4-bis-[4-(2-ethylhexyloxy)-2-hydroxyphenyl]-1,3,5-triazine-benzylidene malonate polysiloxane, glyceryl ethylhexanoate dimethoxycinnamate, disodium-2,2'-dihydroxy-4,4'-dim ethoxy-5,5'-disulfobenzophenone, dipropylene glycol salicylate, sodium hydroxymethoxybenzophenone sulfonate, 4,4',4-(1,3,5-triazine-2,4,6-triyltriimino)-tris-benzoic acid tris(2-ethylhexyl ester), 2,4-bis-[{(4-(2-ethylhexyloxy)-2-hydroxy}phenyl]-6-(4-methoxyphenyl)-1,3,5-triazine, 2,4-bis-[{(4-(3-sulfonato)-2-hydroxypropyloxy)-2-hydroxy}phenyl]-6-(4-methoxyphenyl)-1,3,5-triazine sodium salt, 2,4-bis-[{(3-(2-propyloxy)-2-hydroxypropyloxy)-2-hydroxy}phenyl]-6-(4-methoxyphenyl)-1,3,5-triazine, 2,4-bis-[{4-(2-ethylhexyloxy)-2-hydroxy}phenyl]-6-[4-(2-methoxyethyl carbonyl)phenylamino]-1,3,5-triazine, 2,4-bis-[{4-(3-(2-propyloxy)-2-hydroxypropyloxy)-2-hydroxy}phenyl]-6-[4-(2-ethylcarboxyl) phenylamino]-1,3,5-triazine, 2,4-bis-[{4-(2-ethylhexyloxy)-2-hydroxy}phenyl]-6-(1-methylpyrrol-2-yl)-1,3,5-triazine-2,4-bis-[{4-tris-(trimethylsiloxysilylpropyloxy)-2-hydroxy}phenyl]-6-(4-methoxyphenyl)-1,3,5-triazine, 2,4-bis-[{4-(2''-methylpropenyloxy)-2-hydroxy}phenyl]-6-(4-methoxyphenyl)-1,3,5-triazine, 2,4-bis-[{4-(1',1',1',3',5',5',5'-heptamethylsiloxy-2''-methylpropyloxy)-2-hydroxy}phenyl]-6-(4-methoxyphenyl)-1,3,5-triazine, 2-(4-diethylamino-2-hydroxybenzoyl)benzoic acid hexyl ester and indanylidene compounds.

The perfumes e) viii) include any perfume commonly used in cosmetic, hygienic, medical or household cleansing articles. Examples of the perfumes are thymol, eugenol, vanillin, citronellal, terpinyl acetate, citronellol and beta-pinene, citral, geraniol, nerol, perillaldehyde, alpha-terpineol, dodecanol and L-carvone.

The fragrances e) viii) include for example alpha-hexylcinnamaldehyde, p-tert-butyl cyclohexyl acetate, cis-3-hexenyl acetate, allyl amyl glycolate, coumarin, dihydromyrcenol (2,6-dimethyl-7-octen-2-ol), methyl dihydrojasmonate alpha-hexylcinnamaldehyde, p-tert-butyl cyclohexyl acetate, cis-3-hexenyl acetate, allyl amyl glycolate, coumarin, dihydromyrcenol (2,6-dimethyl-7-octen-2-ol), methyl dihydrojasmonate, 4,6,6,7,8,8-hexamethyl-1,3,4,6,7,8-hexahydrocyclopenta[g]benzopyran, tetrahydrolinalool (3,7-dimethyloctan-3-ol), benzyl salicylate, 2-methyl-3-(4-tert-butyl-phenyl)propanal, cinnamic alcohol, 4,7-methano-3a,4,5,6,7,7a-hexahydro-5-indenyl acetate and/or 4,7-methano-3a,4,5,6,7,7a-hexahydro-6-indenyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene, hexyl salicylate, 4-tert.-butylcyclohexyl acetate, 2-tert.-butylcyclohexyl acetate, alpha-ionone (4-(2,2,6-trimethyl-2-cyclohexen-1-yl)-3-buten-2-one), terpinyl acetate, 4-(4-hydroxy-4-methylpentyl)-3-cyclohexene carboxaldehyde, alpha-amylcinnamaldehyde, 15-pentadec-11-enolide and/or 15-pentadec-12-enolide, 15-cyclopentadecanolide, 1-(5,6,7,8-tetrahydro-3,5,5,6,8,8-hexamethyl-2-naphthalenyl)ethanone, 2-ethyl-4-(2,2,3-trimethyl-3-cyclopenten-1-yl)-2-buten-1-ol, menthol, anethole, geraniol, linalool, citronellol, linalyl acetate, 2-phenylethyl alcohol, rose oxide (4-methyl-2-(2-methyl-1-propenyl)tetrahydropyran), allyl heptanoate, 4-methylacetophenone, 1-(2,2,6-trimethylcyclohexyl)hexan-3-ol, 2,4,6-trimethyl-4-phenyl-1,3-dioxane, benzylacetone, methyl cinnamate, ethylene brassylate, 3a,6,6,9a-tetramethyldodecahydronaphtho[2,1-b]furan.

The dyes and pigments e) ix) include any cationic or anionic dyes and pigments commonly used to color articles for cosmetic, hygienic, medical or household cleansing uses. Examples of such pigments are titanium dioxide, iron oxide, zinc oxide, zirconium oxide, cerium oxide and the respective oxides coated with alumina or aluminum stearate.

The hydrophilic components or polymers e) x) include any hydrophilic or water-soluble component to help solubilize and/or physically stabilize the other components in the composition. A hydrophilic material is typically a compound that has solubility in water of at least 7 wt-% (25° C.). Examples of the hydrophilic component are polyhydric alcohols, lower alkyl ethers (i.e., having a sufficiently small number of carbon atoms to meet the solubility limit above), N-methylpyrrolidones and alkyl esters. Suitable polyhydric alcohols (i.e., organic compounds having three or more hydroxyl or ether groups) have a molecular weight of less than 500, preferably less than 400, and more preferably less than 200. Examples of polyhydric alcohols include, but are not limited to, glycerol, polypropylene glycol, polyethylene glycol, pentaerythritol, trimethylolpropane, trimethylolethane, trimethylolbutane, sorbitol, mannitol, xylitol, pantothenol, ethylene glycol adducts of polyhydric alcohol, propylene oxide adducts of polyhydric alcohol, diglycerine, polyglycerine, erythritol, sorbitan, sugars (e.g., sucrose, glucose, fructose, mannose, xylose, saccharose), sugar alcohols, and the like.

The inventive aqueous composition can also include one or more hydrophobic compounds. Such hydrophobic compounds are commonly referred to as emollients (component e) xi). The emollients include hydrophobic compounds, which are usually different from the silicone polymers as used in the aqueous composition explained above (or used in addition to them, respectively), and preferably exhibit a solubility in water of less than 5 wt-% (25° C.), preferably less than 1 wt-% (25° C.). Examples of emollients include, but are not limited to, short chain (i.e, C1-06) alkyl or (C6-C12)aryl esters of long (i.e., C8-C36) straight or branched chain alkyl or alkenyl alcohols or acids and polyethoxylated derivatives of the alcohols; short chain (i.e., C1-06) alkyl or (C6-C12)aryl esters of (C4-C12)diacids or (C4-C12)diols optionally substituted in available positions by —OH; (C2-C18)alkyl or (C6-C12)aryl esters of glycerol, triglycerides, pentaerythritol, ethylene glycol, propylene glycol, as well as polyethoxylated derivatives of these; (C12-C22)alkyl esters or (C12-C22)ethers of polypropylene glycol; (C12-C22)alkyl esters or (C12-C22)ethers of polypropylene glycol/polyethylene glycol copolymer. Additional examples of hydrophobic components include long chain (i.e., C8-C36) alkyl and alkenyl esters of long (i.e., C8-C18) straight or branched chain alkyl or alkenyl alcohols or acids, long chain (i.e., C8-C36) alkyl and alkenyl amides of long straight or branched chain (i.e., C8-C36) alkyl or alkenyl amines or acids; hydrocarbons including straight and branched chain alkanes and alkenes such as isoparafins (e.g. isooctane, isododecane, isooctadecane, etc.), squalene, and mineral oil, (C12-C22)alkyl and (C12-C22)alkenyl alcohols, and petroleum derived alkanes such as isoparaffins, petrolatum, petrolatum USP, as well as refined natural oils such as olive oil NF, cotton seed oil, peanut oil, corn oil, sesame oil, safflower oil, soybean oil, rape seed oil, almond oil, coconut oil, jojoba oil, orange oil, peach seed oil, apricot seed oil, and the like, and blends thereof.

The organic polymeric quaternary ammonium compounds e) xii) include cationic polymers based upon cellulose, starch or guar derivatives such as cationic polysaccharides, cationic cellulose derivatives such as Polyquaternium-10, Polyquaternium-24, Polyquaternium-67 and Polyquaternium-72. Also included are Guar derivatives such as Guar Hydroxypropyltrimonium Choride and cationic guar derivatives sold by the Hercules Company under the trade names N-Hance and AquaCat and the Cognis Company under the trade name Cosmedia. Also included are the cationic organic polymers Polyquaternium-2, Polyquaternium-7, Polyquaternium-17, Polyquaternium-18, Polyquaternium-27, and Polyquaternium-39 among others.

The silicone and organic polymer fixatives e) xx) include silicone and organic resins used to film-forming agents and fixatives, in particular in hair care. Examples of silicone fixatives are silicone resins such as polyalkylsilsesquioxane, polymeric resins comprising trimethylsiloxy $(CH_3)_3SiO_{1/2}$, dimethylsiloxy $(CH_3)_2SiO_{2/2}$, methylsiloxy $CH_3SiO_{3/2}$ and $SiO_{4/2}$ groups. Also included are trimethylsilylsilacates such as Belsil TMS 803 sold by Wacker-Chemie.

The antidandruff agents e) xiii) include for example metal pyrithiones. Metal pyrithiones useful herein are heavy metal salts of 1-hydroxy-2-pyridinethione, the heavy metal salts being zinc, tin, cadmium, magnesium, aluminium, barium, bismuth, strontium, copper, and zirconium. Preferred heavy metals are zinc and copper. More preferred metal pyrithione is a zinc salt of 1-hydroxy-2-pyridinethione known in the art as zinc pyrithione. Such metal pyrithione can be suspended by or coated by a polymer. Such polymer can be anionic polymers, nonionic polymers, and any other polymers. It may be preferred to use anionic polymers, more preferably sodium polynaphthalene sulfonate, still more preferably sodium polynaphthalene sulfonate having a molecular weight of about 3,000 g/mol in comparison to standards of sodium poly(styrenesulfonate) and a charge density of about 3.5-4 meq/g.

The antiperspirant e) xiv) includes any commonly used active substance used as an antiperspirant in skin care formulations. Included, but not limited to, salts of aluminum or zirconium as well as their complex with amino acids such as glycine. Included are the salts such as aluminum chlorides, zirconium hydroxychlorides, zirconium oxychlorides, their complexes with polyglycols and mixtures thereof. Preferred are aluminum/zirconium salt-glycine complexes.

The insect repellants e) xv) include any material known to be active in insect control. This includes, but is not limited to, N,N-diethyl-m-toluamide (DEET), p-menthane-3,8-diol (PMD), icaridin, nepetalactone, tricyclodecenyl allyl ether, (3-[N-Butyl-N-acetyl]-aminopropionic acid, ethyl ester, dimethyl phthalate, and indalone.

The vitamins e) xvi) include all vitamins and vitamin precursors. All vitamins and vitamin precursors can be used which are suitable or usual for cosmetic and/or dermatological uses. Examples of the vitamins and vitamin precursors include tocopherols, vitamin A, nicotinic acid and niacinamide, further vitamins of the B complex, in particular biotin, and vitamin C and panthenol and derivatives thereof, in particular the esters and ethers of panthenol and cationically derivatized panthenols, such as e.g. panthenol triacetate, panthenol monoethyl ether and the monoacetate thereof and cationic panthenol derivatives.

As additional components with antimicrobiological properties xix), for example short chain alcohols, different from components a), b) and c) as defined above, preferably with less than 5 carbon atoms and for example parabens may be used, in particular, in the articles of the invention or in the aqueous composition of the invention. More specifically they include e.g. p-hydroxybenzoic acid ester of simple alcohols and include methyl paraben, ethyl paraben, n-propyl paraben and n-butyl paraben. Preferred is the mixture of methyl paraben and ethyl paraben. Preferably parabens are not used in the aqueous compositions of the invention and/or the articles according to the invention. Preferably the aqueous compositions of the invention and/or the articles of the invention contain only components a), b) and c) as defined above as anti-microbiological agents.

As further additional components with antimicrobiological properties xix), for example, isothiazolinones can be used in the aqueous composition of the invention or the articles comprising them, and they include for example substituted derivatives of 1,2-thiazol-3-one and include methylisothiazolinone, chloromethylisothiazolinone, benzisothiazolinone, octylisothiazonline and mixtures thereof. Preferred is methylisothiazolinone, benzisothiazolinone or a mixture thereof. Preferably isothiazolinones are not used in the aqueous compositions of the invention and/or the articles according to the invention.

The botanical extracts xvii) which can be used in the aqueous composition of the invention or the articles comprising them include all botanical extracts of plant materials that have a care function or antimicrobiological properties. Preferred are the botanical extracts including, but are not limited to, grape fruit extract, green tee extract, coconut derived phospholipid, curcumin compounds, pomegranate seed oil extract, lemongrass oil, cinnamon oil, citrus extract, basil, citronella, thyme, *eucalyptus*, oregano, peppermint, clove extracts or menthol, thymol, and eucalyptol among others. Particularly preferred are tetrahydrocurcumin, tetrahydrodemethoxycurcumin, tetrahydrobisdemethoxycurcumin and mixtures thereof.

The inorganic or polymeric thickeners e) xviii) or d) vii) which can be used in the aqueous composition of the invention or the articles comprising them include in particular swellable polymers. Swellable polymers, which are slightly crosslinked, function as viscosifiers in aqueous solvent systems. In general, these swellable polymers are preferred because they tend to be far less "slimy" going on and once the hands perspire and are exposed to water after treatment. Excessive crosslinking will result in polymers that do not swell sufficiently to increase the viscosity of the composition. In order to ensure adequate swelling, if a chemical crosslinker is used, the concentration of crosslinker is quite low, e.g., less than about 1000 parts per million (ppm), and preferably less than 500 ppm, based on the weight of the dry polymer. Examples of the swellable polymers include slightly crosslinked acrylate copolymers, polysaccharides such as xanthan gum, and cellulose derivatives such a sodium carboxymethylcellulose.

One class of crosslinked, swellable polymers for use in the compositions of the present invention include acrylamide and at least one other quaternary monomer selected from the group consisting of trialkylaminoalkylacrylate and methacrylate salts, dialkyldiallyl ammonium salts, acrylamidoalkyltrialkyl ammonium salts, methacrylamidoalkyltrialkyl ammonium salts, and monomers that include imidazolinium salts. The counterions are preferably $F^-$, $Cl^-$, $Br^-$, and alkylsulfonate. Other co-monomers may also be added including N-vinyl pyrrolidone, N-vinyl caprolactam, methyl vinyl ether, acrylates, methacrylates, styrene, and the like. A particularly preferred polymer is a poly(2-methacryloxyethyl trimethyl ammonium chloride) polydimethylaminoethyl methacrylate, which conforms to the CTFA designation Polyquaternium 37. Another preferred polymer includes acrylamide and methacryloyloxyethyl trimethyl ammonium chloride, which conforms to the CTFA designation Polyquaternium 32. Other swellable are slightly crosslinked polymers of N-vinyl lactams, such as N-vinyl pyrrolidone. A range of swellable, crosslinked polyvinylpyrrolidone (PVP) materials can be prepared via covalent crosslinking with diallyl maleate or by radiation crosslinking of linear PVP powders. The polymers are also nonionic and have excellent compatibility with cationic components.

The inorganic thickeners include any inorganic materials that can be used as viscosity modifiers in the inventive compositions. These inorganic thickeners include, but are not limited to, clay minerals such a bentonites, kaolinites, montmorillonite, and talc among others.

The organic solvents for one or more of the active ingredients include common organic solvents such as ethanol, isopropanol, 1-butanol, sec-butanol, methylethyl ketone, acetone, toluene, cyclohexanol, cyclohexane, 1,6-hexanediol, ethyl acetate, butyl acetate, and glycols or polyglycols and their ethers, such as tripropylene glycol or methoxypropanol, butylglycol, butyldiglycol and the like. Short-chain alcohols such as ethanol, isopropanol, 1-butanol and sec-butanol are commonly used and can improve the antimicrobiological properties of the cosmetic, hygienic, medical or household cleansing article.

The pH adjusting agents d) ix) which can be used in the aqueous composition of the invention or the articles comprising them include any acids and bases commonly used in cosmetic, hygienic, medical or household cleansing articles. The pH adjusting agents include the non-limiting examples, the inventive organic acids or polymeric organic acids cited above, inorganic acids such as sulfuric or phosphoric acids, organic bases such as sodium hydroxide, potassium hydroxide, sodium bicarbonate or sodium carbonate, sodium or potassium salts of sulfuric or phosphoric acids, as well as amine type bases such trimethylamine, ethanolamine, diethanolamine, triethanolamine, and dibutylethanolamine. The home care articles, fabric articles, cosmetic articles, hygienic articles, medical articles, personal care articles, and household articles such as cleansing article comprising the inventive aqueous composition of one or more silicone polymers providing multiple benefits in use.

The silicone polymers are well recognized to provide care benefits in application to hair or skin. Silicone polymers, in particular polydimethylsiloxanes, aminosilicones and quaternized silicones are well recognized to provide benefits such as those attributed to emollients, they provide gloss or shine, body and volume to hair. Additionally, they help to provide thermal protection, color retention and contribute to hair repair or hair restoration. The silicone polymers polydimethylsiloxanes, aminosilicones and quaternized silicones are commonly used in hair conditioners and shampoos to reduce the friction between hairs, reduce the force needed to comb hair and repair damaged hair surfaces. It is well recognized that these and other benefits in hair and skin care can be enhanced by combinations of the inventive silicone polymers and the components a), b), c), d) or e). In particular, the components a), b) and c) with 6 or more carbon atoms enhance the emollient or humectant characteristics of silicone polymers and can lead to an increase in hair shine, body and volume. Combinations of the silicone polymers and components a), b), c) and e) can also significantly improve the repair of damaged hair.

The silicone polymers, in particular polydimethylsiloxanes, aminosilicones and quaternized silicones, in combination with organic oils and fats as well as volatile silicones are commonly used in skin creams, lotions and washes, hygienic wipes and sunscreens. In these articles, the silicone polymer provides for a smooth feel, helps to hydrate the skin, reduce tack of the formulations and can reduce or hide the effects of ageing. Combinations of the silicone polymers and components a), b), c) d) and e) can also significantly improve the care benefits of these skin creams, lotions and washes, hygienic wipes and sunscreens, including but not limited to the feel, hydration of the skin and tack. The components a), b) and c) can alone or together with the silicone polymers act as emollients or humectants in skin care. The silicone polymers can in combination with the components a), b) and c) improve the effectiveness of UV absorbers, component e) vii), and protect skin from the damaging influence of UV irradiation.

The silicone polymers can in combination with the components a), b) and c) improve the dispersion of dyes and pigments into cosmetic, hygienic, medical or household cleansing articles, improving among other benefits the color, shine and color stability.

The silicone copolyol and quaternized silicone copolyol are commonly used as surfactants in cosmetic, hygienic, medical or household cleansing articles and improve the dispersion of active ingredients and stabilize the articles, for example in antiperspirants and deodorants. Combinations of the silicone polymers and the components a), b) or c) can significantly enhance these properties. A number of the inventive components d) and e) can enhance the antimicrobiological properties of the combination of components a), b) and c). Some of the components d) vi) and e) v) used in combination or alone can have antimicrobiological properties at pH values of below 6. Some of the components e) viii) and e) xvii) when used alone, or in particular in combination with the components a), b) and c), are known to exhibit antimicrobiological properties. Some of the components d) ii), e) ii) and e) xii) with quaternary ammonium groups when used alone or in combination are known to exhibit antimicrobiological properties.

In the following the preferred embodiments of the invention are summarized:

1. Embodiment: Aqueous composition comprising one or more silicones, and
a) at least one compound of the general formula (1)

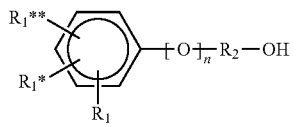

(1)

wherein
n is 0 or 1,
$R_1$, $R_1^*$ and $R_1^{**}$ are independently selected from the group consisting of hydrogen, a linear or branched C1-C9 alkyl group, and a linear or branched C1-C9 alkyloxy group, and
$R_2$ is a linear or branched divalent C2-C5 alkyl group,
and
b) at least one compound selected from the group consisting of the general formulae (2) and (3)

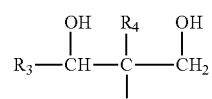

(2)

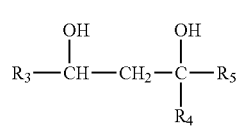

(3)

wherein compounds (2) and (3) each have 5 to 22 carbon atoms, preferably 6 to 22 carbon atoms, and wherein
$R_3$ is selected from the group consisting of hydrogen, a linear or branched C1 to C12 alkyl group, a linear or branched C1 to C12 alkylaryl group, an aryl group, a linear or branched C1 to C12 alkyloxy group, a linear or branched 01 to C12 alkylaryloxy group, and an aryloxy group, and
$R_4$ and $R_5$ are the same or different and are selected from the group consisting of a linear or branched C1 to C12 alkyl group, a linear or branched 01 to C12 alkylaryl group, an aryl group, or
$R_4$ and $R_5$ together form an optionally substituted ring system with at least 5 carbon atoms, and
c) optionally one or more compounds selected from the group consisting of the general formulae (4) and (5)

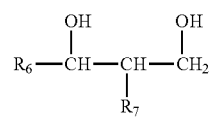

(4)

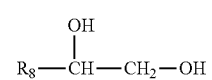

(5)

wherein
$R_6$ and $R_7$ are either both hydrogen or one is a methyl group and the other is hydrogen and $R_8$ is selected from the group consisting of a linear or branched C6 to C14 alkyl group, a linear or branched C6 to C14 alkyloxy group, a linear or branched C6 to C14 alkyloxyalkyl group, a linear or branched C6 to C14 alkylaryl, a linear or branched C6 to C14 alkylaryloxy and aryloxy group.

2. Aqueous composition according to embodiment 1, comprising
d) one or more substances selected from the group consisting of
   i) nonionic surfactants,
   ii) cationic surfactants,
   iii) anionic surfactants,
   iv) amphoteric surfactants, v) oily phase-forming substance, preferably selected from saturated and unsaturated fatty oils and fats with between 8 and 32 carbon atoms,
vi) organic acids and polymeric derivatives thereof,
vii) inorganic or polymeric thickeners,
viii) antioxidants, and
ix) pH adjusting agents.

3. Aqueous composition according to embodiments 1 or 2, comprising at least one surfactant.

4. Aqueous composition according to any of the preceding embodiments, comprising components a) and b) in a quantity producing a synergistic antimicrobial effect.

5. Aqueous composition according to any of the preceding embodiments, wherein the total weight of the sum of the components a), b) and c) is from 0.5 to 12 weight-%, preferably from 1.0 to 10 weight-%, more preferably from 1.5 to 7.5 weight-%, still more preferably from 1.5 to 5.0 weight-% based on the total weight of the aqueous composition.

6. Aqueous composition according to any of the preceding embodiments, wherein the amount of the one or more silicones is in the range of 1 and 50 weight-%, preferably between 5 and 40 weight-%, and more preferably between 10 and 30 weight-% based on the total weight of the aqueous composition.

7. Aqueous composition according to any of the preceding embodiments, and wherein the composition is in the form of an emulsion, preferably selected from a microemulsion or an oil-in-water emulsion.

8. Aqueous composition according to any of the preceding embodiments, which is free of parabens.

9. Aqueous composition according to any of the preceding embodiments, wherein the silicones are selected from the group consisting of polyorganosiloxanes which optionally may have one or more functional groups, preferably said silicones are selected from polydimethylsiloxanes, amino group-modified silicones, polyether group-modified silicones, and silicones comprising at least one quaternary ammonium group and mixtures thereof.

10. Aqueous composition according to any of the preceding embodiments, wherein the silicone is selected from linear or branched polydimethylsiloxanes with a viscosity equal to or greater than 350 mPa*s at 25° C. determined according to DIN 53015.

11. Aqueous composition according to any of the preceding embodiments, wherein the silicone polymer is an amino group-modified silicone selected from the group consisting of linear or branched polydimethylsiloxanes having at least one aminoalkyl group, preferably selected from the group consisting of terminal and pendant aminopropyl and/or aminoethylaminopropyl groups, having preferably 0.1 to 0.9 mmol/g amino functionality.

12. Aqueous composition according to any of the preceding embodiments, wherein the silicone is selected from the group consisting of a silicone comprising at least one quaternary ammonium group, preferably selected from the group consisting of silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-17, silicone quaternium-18, silicone quaternium-20, silicone quaternium-21, silicone quaternium-22, silicone quaternium-25, and silicone quaternium-26, and mixtures thereof.

13. Aqueous composition according to any of the preceding embodiments, comprising 0.1 to 5.0 weight-%, preferably 0.1 to 3.0 weight-%, more preferably 0.1 to 2.0 weight-% of the total weight of the components a) based on the total weight of the aqueous composition.

14. Aqueous composition according to any of the preceding embodiments, wherein the component a) is selected from the group consisting of 2-phenoxyethanol, 2-phenylethanol or 3-phenylpropanol and a derivative thereof, wherein in said derivative $R_1$ is a C1-C9 alkyl group or a methoxy group and $R_1^*$ and $R_1^{**}$ are each hydrogen, and mixtures thereof, preferably component a) is 2-phenoxyethanol and/or 3-phenyl-1-propanol.

15. Aqueous composition according to any of the preceding embodiments, comprising 0.1 to 5.0 weight-% preferably 0.1 to 3.0 weight-%, more preferably 0.1 to 2.0 weight-% of the total weight of the components b) based on the total weight of the aqueous composition.

16. Aqueous composition according to any of the preceding embodiments, wherein the component b) is selected from the group consisting of 2-methyl-2,4-pentanediol, 2-methyl-2,4-hexanediol, 2,2-dimethyl-1,3-propanediol, 2-methyl-2-propyl-1,3-propanediol, 2,2-dibutyl-1,3-propanediol, 2-butyl-2-ethyl-1,3-propanediol and 2,2-dioctyl-1,3-propanediol, and mixtures thereof, preferably component b) is selected from 2-butyl-2-ethyl-1,3-propanediol, 2-methyl-2,4-hexanediol, and 2-methyl-2-propyl-1,3-propanediol.

17. Aqueous composition according to any of the preceding embodiments, comprising 0.1 to 5.0 weight-%, preferably 0.1 to 3.0 weight-%, more preferably 0.1 to 2.0 weight-% of the total weight of the components c) based on the total weight of the aqueous composition.

18. Aqueous composition according to any of the preceding embodiments, wherein the component c) is selected from the group consisting of 1,2-octanediol, 1,2-decanediol, 3-(2-ethylhexyloxy)-1,2-propanediol, 1,2-dodecanediol, 2-methyl-1,3-propanediol, 1,3-propanediol and 1,3-butanediol, and mixtures thereof, preferably component c) is selected from (3-(2-ethylhexyloxy)-1,2-propanediol, 1,3-propanediol, 1,2-dodecanediol, and 2-methyl-1,3-propanediol.

19. Aqueous composition according to any of the preceding embodiments, comprising 0.4 to 2.0 weight-% of the total of components a) and 0.1 to 5.0 weight-% of the total of components b), each percentage being based on the total weight of the aqueous composition.

20. Aqueous composition according to any of the preceding embodiments, comprising 0.4 to 2.0 weight-% of the total of components a), 0.1 to 5.0 weight-% of the total of components b) and 0.1 to 5.0 weight-% of the total of components c), and wherein the sum of the total of components b) and c) equals 0.2 to 6.0 weight-%), each percentage being based on the total weight of the aqueous composition.

21. Use of the aqueous composition according to any of the preceding embodiments for the manufacture of an article selected from group of homecare articles, household articles, industrial articles, fabric articles, cosmetic articles, hygienic articles, and medical articles.

22. A process for the preparation of the aqueous compositions according to any of the preceding embodiments, comprising the steps of:
(a) mixing one or more of the components a) and b) and optionally one or more component c),
(b) adding one or more silicones,
(c) then adding water, and (d) optionally adding at least one or more components d) in one or more additional process steps to prepare the aqueous composition.

23. Articles comprising at least one aqueous composition according to any of the preceding embodiments, selected from homecare articles, fabric articles, cosmetic articles, hygienic articles, medical articles, personal care articles, and household articles.

24. Articles according to embodiment 23, comprising 0.01 to 30 weight-% of one or more silicones and 0.01 to 10 weight-% of the total of the components a), b) and optionally c), based on the total weight of the article.

25. Articles according to embodiments 23 or 24, comprising 0.5 to 10 weight-% of one or more silicone polymers and 0.2 to 5 weight-% of the total of the components a), b) and optionally c).

26. Articles according to any of embodiments 23 to 25, comprising e) one or more functional components, including:
i) volatile silicone compounds,
ii) anionic, nonionic, cationic or amphoteric surfactants,
iii) oily phase-forming substance, preferably selected from saturated and unsaturated fatty oils and fats with between 8 and 32 carbon atoms,
iv) saturated and unsaturated aliphatic alcohols, different from components a), b) and c) as defined in embodiment 1,
v) organic acids and polymeric derivatives thereof,
vi) antioxidants,
vii) UV absorbers,
viii) perfumes and fragrances,
ix) dyes and pigments,
x) hydrophilic components or polymers,
xi) emollients,
xii) organic polymeric quaternary ammonium compounds,
xiii) antidandruff agents,
xiv) antiperspirants,
xv) insect repellants,
xvi) vitamins or vitamin precursors,
xvii) botanical extracts,
xviii) inorganic or polymeric thickeners,
xix) additional components with antimicrobiological properties, preferably selected from the group consisting of short chain alcohols, different from components a), b) and c) as defined in embodiment 1,
xx) silicone and organic polymer fixatives, and
xxi) organic solvents.

27. Articles according to any of embodiments 23 to 26, which are an oil-in-water emulsion, a dispersion, a microemulsion, or a water-in-oil cream.

28. A method for the cosmetic, hygienic, medical or cleansing treatment which comprises the application of the articles according to any of embodiments 23 to 27 to at least one substrate, preferably selected from skin, hair, household and industrial goods.

29. A method of preserving aqueous compositions comprising at least one silicone by adding a mixture of components a) and b), and optionally component c), as defined in any of the preceding embodiments.

30. Use of a mixture of components a) and b), and optionally component c), as defined in any of the preceding embodiments for preserving aqueous compositions comprising at least one silicone against microorganism, such as bacteria, yeasts, and particularly molds and fungi.

31. A method for preserving aqueous compositions comprising at least one silicone against microorganism, which comprises adding a mixture of components a) and b), and optionally component c), as defined in any of the preceding embodiments, to said aqueous compositions comprising the at least one silicone.

32. A preservative composition comprising a mixture of components a) and b) and optionally component c) as defined in any of the preceding embodiments.

The present invention is further illustrated by the following examples.

EXAMPLES

Unless otherwise stated differently, all percentages given are weight percent related to the total weight of the compositions. In particular, the percentages for components a), components b), and components c) are weight percentages related to the total weight of the compositions. The "parts" used below for the different components in the examples are weight parts.

The testing of microbiological stability is performed according to the state-of-the-art in that the composition according to the invention is inoculated with 1.0 weight-% of a suspension of microorganisms with $10^4$-$10^8$ KBE/ml ("KBE=Koloniebildende Einheiten je ml" (colony forming units (cfu) per ml of the sample)) of live bacteria, yeasts or fungi. The mixture is thoroughly mixed then incubated at 25+/−2° C. in air.

After incubation for a period of time ranging from 7 to 36 days, a sample of the inoculated emulsion is swabbed onto agar plates of growth medium (caseinpepton-sojapepton-agar for bacteria and sabouraud-dextrose-agar for yeasts and fungi). The agar plates are then incubated at 26+/−2° C. for three days, after which time the plates are inspected for colonies of microbiological growth.

The results of the microbiological stress tests are summarized in the Tables 1-4 and denoted as: 0 (no growth), X (minimal growth, less than 5 colonies), XX (moderate growth 5-10 colonies), XXX (strong growth, >10 colonies).

In some cases, all the microorganisms in the inoculated emulsion are only killed after a number of days incubation. This is indicated in the tables as the number of days to destruction of all microorganisms.

Viscosities are determined at 25° C. (unless indicated otherwise) according to the method of Höppier (DIN 53015: Viscometry—Measurement of viscosity by means of the rolling ball viscometer by Floppier).

Solids content is determined using an infrared moisture analyzer model HR73 as sold by Mettler Toledo GmbH (Gießen, Germany).

Color according to Hazen is determined with a LICO 200 Color Analyzer as sold by HachLange GmbH (Weinheim, Germany).

Example 1

An aqueous microemulsion comprising 20% of an amino group-modified silicone with aminoethylaminopropyl pendant groups and an amino content of 0.77 mmol $NH_2$/g and 19.3% of a mixture of an alkylpolyglycoside and cocosamidopropyl betaine surfactants, was prepared by first mixing 50 parts of the aminosilicone with
2.25 parts (0.9%) of 2-phenoxyethanol (component a)),
3.75 parts (1.5%) of 2-butyl-2-ethyl-1,3-propanediol (component b)), and
1.5 parts (0.6%) ethylhexyl glycerin (component c)),
then adding this mixture to a solution of the 87.5 parts Plantacare 2000 UP (a 50% aqueous solution of C8-C16 alkylpolyglycosides sold by the BASF SE, Ludwigshafen, Germany) and 15.0 parts of Genagen CAB 818 (a 30% aqueous solution of cocosalkylamidopropylbetaine sold by the Clariant GmbH, Frankfurt am Main, Germany) in 84.23 parts water and adjusting the pH with 3.0 parts L-arginine and 2.77 parts acetic acid, the remainder being water, in accordance with WO2011042409. The final microemulsion had a viscosity of 18.3 mPa*s at 25° C., a solids content of 43.5%, a color according to Hazen of 190 and a pH value of 8.

The microemulsion exhibited no microbiological growth upon incubation at 25+/−2° C. for 6, and 13 days after inoculation with 1.0% of a suspension with a titer of $10^8$ KBE/ml, comprising a mixture of Gram negative and Gram positive bacteria including *Pseudomonas aeruginosa*, *Pseudomonas putida*, *Burkholderia cepacia*, *Klebsiella pneumonia*, *Enterobacter gergoviae*, *Straphylocuccus aureus* and *Straphylocuccus epidermidis*. In a separate test, the microemulsion exhibited no microbiological growth upon incubation at 25+/−2° C. for 14 and 28 days after inoculation with 1.0% of a suspension of microorganisms with a titer of $10^7$ KBE/ml microorganisms, comprising a mixture of yeasts including *Cadida albicans* and *Cadida parapsilosis*. In a third test the emulsion exhibited no microbiological growth upon incubation at 25+/−2° C. for 14 and 28 days after inoculation with 1.0% of a suspension of microorganisms with a titer of $10^7$ KBE/ml microorganisms, comprising the fungi *Aspergillus brasiliensis*, and *Penicillium pinophilum*.

Comparative Example 1

A microemulsion was prepared as in Example 1, but instead adding
2.25 parts (0.9%) 2-phenoxyethanol (component a)) and
1.5 parts (0.6%) ethylhexyl glycerin (component c)),
but no component b), to the preformed microemulsion, and the blend mixed at ambient temperature until clear.

The microemulsion exhibited no microbiological growth upon incubation at 25+/−2° C. for 6, and 13 days after inoculation with 1.0% of a suspension of with a titer of $10^8$ KBE/ml, comprising a mixture of Gram negative and Gram positive bacteria as in Example 1. In a separate test, the emulsion exhibited no microbiological growth upon incubation at 25+/−2° C. for 14 and 28 days after inoculation with 1.0% of a suspension of microorganisms with a titer of $10^7$ KBE/ml microorganisms, comprising a mixture of yeasts including *Cadida albicans* and *Cadida parapsilosis*. In a third test the emulsion exhibited moderate microbiological growth upon incubation at 25+/−2° C. for 14 and 28 days after inoculation with 1.0% of a suspension of microorganisms with a titer of $10^7$ KBE/ml microorganisms, comprising *Aspergillus brasiliensis*, and *Penicillium pinophilum*.

Example 2

A microemulsion comprising 20% of a silicone polymer comprising at least one quaternary ammonium group, Silicone Quaternium-18, and 10% of a mixture of nonionic surfactants was prepared by first mixing 20 parts of the silicone quat polymer as a microemulsion with 10 parts of the non-ionic surfactants and then adding 70 parts of water and mixed at ambient temperature until clear. The final unpreserved emulsion had a viscosity of 17.8 mPa*s at 25° C., a solids content of 30.3%, a pH value of 8.0 and a color according to Hazen of 71.

To 95.7 parts of this microemulsion were added
3.3 parts (3.3%) 2-phenoxyethanol (component a)),
1.0 part (1.0%) 2-butyl-2-ethyl-1,3-propanediol (component b))
and mixed at ambient temperature until clear. The microemulsion exhibited moderate microbiological growth upon incubation at 25+/−2° C. for 7 days, but no microbiological growth 14 days, after inoculation with 1.0% of a suspension of microorganisms with a titer of $10^5$ KBE/ml microorganisms, comprising *Aspergillus niger*, and *Penicillium funiculosum*.

Comparative Example 2

To 95.7 parts of the microemulsion in Example 2 was instead added
4.3 parts (4.3%) 2-phenoxyethanol (component a)),
but no component (b), and mixed at ambient temperature until clear. The microemulsion exhibited strong to moderate microbiological growth upon incubation at 25+/−2° C. for 7 and 14 days, but no microbiological growth 28 days, after inoculation with 1.0% of the suspension of microorganisms used in Example 2.

Comparative Example 3

To 95.7 parts of the microemulsion in Example 2 was instead added
4.3 parts (4.3%) 2-butyl-2-ethyl-1,3-propanediol (component b)),
but no component a), and mixed at ambient temperature until clear. The microemulsion exhibited strong microbiological growth upon incubation at 25+/−2° C. for 7, 14, 28 and 36 days after inoculation with 1.0% of the suspension of microorganisms used in Example 2.

Example 3

To 95.7 parts of the microemulsion in Example 2 were instead added
1.0 part (1.0%) 3-phenyl-1-propanol (component a)),
3.3 parts (3.3%) 2-butyl-2-ethyl-1,3-propanediol (component b))
and mixed at ambient temperature until clear. The microemulsion exhibited moderate microbiological growth upon incubation at 25+/−2° C. for 7 days, but no microbiological growth 14 and 28 days, after inoculation with 1.0% of the suspension of microorganisms used in Example 2.

Example 4

To 95 parts of the microemulsion in Example 2 were instead added
0.9 parts (0.9%) 2-phenoxyethanol (component a)),
3.1 parts (3.1%) 2-butyl-2-ethyl-1,3-propanediol (component b)), and
1.0 part (1.0%) 2-methyl-2-propyl-1,3-propanediol (component b)) and mixed at ambient temperature until clear. The microemulsion exhibited no microbiological growth upon incubation at 25+/−2° C. for 7, 14 and 28 days after inoculation with 1.0% of the suspension of microorganisms used in Example 2.

Comparative Example 4

To 95 parts of the microemulsion in Example 2 were instead added
0.9 parts (0.9%) 2-phenoxyethanol (component a)),
2.1 parts (2.1%) ethylhexylglycerin (component c)), and
2.0 parts (2.0%) 1,2-octanediol (component c)),
but no component (b), and mixed at ambient temperature until clear. The microemulsion exhibited strong microbiological growth upon incubation at 25+/−2° C. for 7, 14 and 28 days after inoculation with 1.0% of the suspension of microorganisms used in example 2.

Example 5

To 95 parts of the microemulsion in Example 2 were instead added
0.9 parts (0.9%) 2-phenoxyethanol (component a)),
2.0 parts (2.0%) 2-butyl-2-ethyl-1,3-propanediol (component b)),
0.5 parts (0.5%) 2-methyl-1,3-propanediol (component c)),
0.5 parts (0.5%) 1,3-propanediol (component c)), and
1.1 parts (1.1%) ethylhexyl glycerin (component c)) and mixed at ambient temperature until clear. The microemulsion exhibited minor microbiological growth upon incubation at 25+/−2° C. for 7 days, but no microbiological growth 14 and 28 days, after inoculation with 1.0% of the suspension of microorganisms used in Example 2.

Comparative Example 5

To 97 parts of the microemulsion in Example 2 were instead added
0.9 parts (0.9%) 2-phenoxyethanol (component a)),
0.5 parts (0.5%) 2-methyl-1,3-propanediol (component c)),
0.5 parts (0.5%) 1,3-propanediol (component c)), and
1.1 parts (1.1%) ethylhexyl glycerin (component c)), but no component (b), and mixed at ambient temperature until clear. The microemulsion exhibited strong to moderate microbiological growth upon incubation at 25+/−2° C. for 7 and 14 days, and minimal growth 28 days after inoculation with 1.0% of the suspension of microorganisms used in Example 2.

Comparative Example 6

To 95.9 parts of the microemulsion in Example 2 were instead added
2.0 parts (2.0%) 2-butyl-2-ethyl-1,3-propanediol (component b)),
0.5 parts (0.5%) 2-methyl-1,3-propanediol (component c)),
0.5 parts (0.5%) 1,3-propanediol (component c)), and
1.1 parts (1.1%) ethylhexyl glycerin (component c)),
but no component (a), and mixed at ambient temperature until clear. The microemulsion exhibited strong to moderate microbiological growth upon incubation at 25+/−2° C. for 7, 14 and 28 days after inoculation with 1.0% the suspension of microorganisms used in example 2.

Example 6

A microemulsion comprising 20% of an amino group-modified silicone with aminoethylaminopropyl pendant groups and an amino content of 0.77 mmol $NH_2$/g was prepared as in Example 1 but without first mixing the aminosilicone with any component a), b) or c). The microemulsion had a viscosity of 27.1 mPa*s at 25° C., a solids content of 42.5%, a color according to Hazen of 222 and a pH value of 8.5. To 95 parts of this microemulsion were added
0.9 parts (0.9%) 2-phenoxyethanol (component a)),
3.1 parts (3.1%) 2-butyl-2-ethyl-1,3-propanediol (component b)), and
1.0 part (1.0%) 2,2-dimethyl-1,3-propanediol (component b))
and mixed at ambient temperature until clear. The microemulsion exhibited no microbiological growth upon incubation at 25+/−2° C. for 7 and 14 days after inoculation with 1.0% of a suspension of microorganisms with a titer of $10^4$ KBE/ml microorganisms, comprising *Aspergillus niger*, and *Penicillium funiculosum*.

Example 7

To 96.0 parts of the microemulsion comprising 20% of an amino group-modified silicone in Example 6, but without any component a), b) or c), were instead added
0.9 parts (0.9%) 2-phenoxyethanol (component a)),
2.0 Parts (2.0%) 2-butyl-2-ethyl-1,3-propanediol (component b)), and
1.1 parts (1.1%) ethylhexyl glycerin (component c))
to the emulsion and mixed until clear. The microemulsion exhibited minor microbiological growth upon incubation at 25+/−2° C. for 7 and 14 days, but no microbiological growth 24 days after inoculation with 1.0% of the suspension of microorganisms used Example 6.

Example 8

To 97.5 parts of the microemulsion comprising 20% of an amino group-modified silicone in Example 6, but without any component a), b) or c), were instead added
0.9 parts (0.9%) 2-phenoxyethanol (component a)) and
1.6 parts (1.6%) 2-butyl-2-ethyl-1,3-propanediol (component b)).
The microemulsion exhibited minor microbiological growth upon incubation at 25+/−2° C. for 14 and 24 days, but no microbiological growth 36 days after inoculation with 1.0% of the suspension of the microorganisms used in Example 6.

Example 9

To 97.5 parts of the microemulsion comprising 20% of an amino group-modified silicone in Example 6, but without any component a), b) or c), were instead added
2.0 parts (2.0%) 2-phenoxyethanol (component (a)) and
0.5 parts (0.5%) 2-methyl-2,4-hexanediol (component (b)).
The microemulsion exhibited moderate microbiological growth upon incubation at 25+/−2° C. for 7 days, but no microbiological growth 14 and 24 days, after inoculation with 1.0% of the suspension of microorganisms as used in Example 6.

Comparative Example 7

To 97.5 parts of the microemulsion comprising 20% of an amino group-modified silicone in Example 6, but without any component a), b) or c), was instead added
2.5 parts (2.5%) 2-phenoxyethanol (component a))
but no component (b). The microemulsion exhibited moderate microbiological growth upon incubation at 25+/−2° C. for 7 and 14 days, but no microbiological growth 28 days after inoculation with 1.0% of the suspension of microorganisms used in Example 6.

Comparative Example 8

To 97.5 parts of the microemulsion comprising 20% of an amino group-modified silicone in Example 6, but without any component a), b) or c), was instead added
2.5 parts (2.5%) 2-butyl-2-ethyl-1,3-propanediol (component b)),
but no component (a). The microemulsion exhibited strong to moderate microbiological growth upon incubation at 25+/−2° C. for 7, 14 and 28 days after inoculation with 1.0% of the suspension of microorganisms used in Example 6.

Comparative Example 9

To 98 parts of the microemulsion comprising 20% of an amino group-modified silicone in Example 6, but without any component a), b) or c), were instead added
0.9 parts (0.9%) 2-phenoxyethanol (component (a)) and
1.1 parts (1.1%) ethylhexyl glycerin (component (c)),
but no component b). The microemulsion exhibited strong to moderate microbiological growth upon incubation at 25+/−2° C. for 14 and 28 days after inoculation with 1,0% of the suspension of microorganisms used in Example 6.

Comparative Example 10

To 95 parts of the microemulsion comprising 20% of an amino group-modified silicone in Example 6, but without any component a), b) or c), were instead added
0.9 parts (0.9%) 2-phenoxyethanol (component a)),
1.75 (1.75%) ethylhexyl glycerin, and
2.35 parts (2.35%) 1,2-octanediol (both components c)),
but no component b). The microemulsion exhibited strong to moderate microbiological growth upon incubation at 25+/−2° C. for 7, 14 and 28 days, but no microbiological growth 36 days, after inoculation with 1.0% of the suspension of microorganisms used in Example 6.

Example 10

To 95 parts of the microemulsion comprising 20% of an amino group-modified silicone in Example 6, but without any component a), b) or c), were instead added
0.9 parts (0.9%) 2-phenoxyethanol (component a)),
3.0 parts (3.0%) 2-butyl-2-ethyl-1,3-propanediol (component b)),
0.6 parts (0.6%) ethylhexyl glycerin (component c)) and
0.5 parts (0.5%) 1,3-propanediol (component c))
and mixed at ambient temperature until clear. The microemulsion exhibited no microbiological growth upon incubation at 25+/−2° C. for 7, 14 and 24 days after inoculation with 1.0% of the suspension of microorganisms used in Example 6.

Example 11

To 95 parts of the microemulsion comprising 20% of an amino group-modified silicone in Example 6, but without any component a), b) or c), were added
0.9 parts (0.9%) 2-phenoxyethanol (component a)),
1.5 parts (1.5%) 2,2-dimethyl-1,3-propanediol (component b)),
1.5 parts (1.5%) 2-methyl-2-propyl-1,3-propanediol (component b)),
0.6 parts (0.6%) ethylhexyl glycerin (component c)) and
0.5 parts (0.5%) 1,3-propanediol (component c))
and mixed at ambient temperature until clear. The microemulsion exhibited no microbiological growth upon incubation at 25+/−2° C. for 7, 14 and 28 days after inoculation with 1.0% of the suspension of microorganisms used in Example 6.

Example 12

To 95 parts of the microemulsion comprising 20% of an amino group-modified silicone in Example 6, but without any component a), b) or c), were added
0.9 parts (0.9%) 2-phenoxyethanol (component a)),
3.0 parts (3.0%) 2-methyl-2,4-hexanediol (component b)),
0.6 parts (0.6%) ethylhexyl glycerin (component c)) and
0.5 parts (0.5%) 1,3-propanediol (component c))
and mixed at ambient temperature until clear. The microemulsion exhibited no microbiological growth upon incubation at 25+/−2° C. for 14 and 28 days after inoculation with 1.0% of the suspension of microorganisms used in Example 6.

Example 13

To 98 parts of an aqueous emulsion comprising 30% of a polydimethylsiloxane with a viscosity of 100 mPa*s at 25° C. and 4.3% of a mixture of non-ionic surfactants with an average HLB value of 15.4 were added
0.9 parts (0.9%) 2-phenoxyethanol (component a)),
1.0 part (1.0%) 2-butyl-2-ethyl-1,3-propanediol (component b)) and
0.1 parts (0.1%) ethylhexyl glycerin (component c))
and mixed at ambient temperature for 1 hour. The microemulsion had a solids content of 39.1%, a viscosity at 25° C. of 13.7 mPa*s, an average particle size of 0.29 microns and a pH value of 4.

The microemulsion exhibited no microbiological growth upon incubation at 25+/−2° C. for 6, and 13 days after inoculation with 1.0% of a suspension of with a titer of $10^8$ KBE/ml, comprising a mixture of Gram negative and Gram positive bacteria including *Pseudomonas aeruginosa, Pseudomonas putida, Burkholderia cepacia, Klebsiella pneumonia, Enterobacter gergoviae, Staphylocuccus aureus* and *Staphylocuccus epidermidis*. In a separate test, the microemulsion exhibited no microbiological growth upon incubation at 25+/−2° C. for 14 and 28 days after inoculation with 1.0% of a suspension of microorganisms with a titer of $10^7$ KBE/ml microorganisms, comprising a mixture of yeasts including *Candida albicans* and *Candida parapsilosis*. In a third test, the microemulsion exhibited no microbiological growth upon incubation at 25+/−2° C. for 14 and 28 days after inoculation with 10% of a suspension of microorganisms with a titer of $10^7$ KBE/ml microorganisms, comprising the fungi *Aspergillus brasiliensis*, and *Penicillium pinophilum*.

Example 14

A typical shampoo formulation was prepared by mixing at ambient temperature 33.3 parts of a 27% aqueous solution of sodium lauryl sulfate, with 10 parts of a 30% aqueous solution of cocosamidopropyl betaine, and 51.7 parts of water and adding 5 parts of the unpreserved silicone microemulsion according to Example 2, comprising 20% of Silicone Quaternium-18, and 10% of a mixture of nonionic surfactants.

To 97 parts of this shampoo formulation were added
1.0 part (1.0%) 3-phenyl-1-propanol (component a)) and
2.0 parts (2.0%) 2-butyl-2-ethyl-1,3-propanediol (component b)).

The shampoo formulation had a viscosity of 14.4 mPa*s at 25° C., a solids content of 28.6%, a pH value of 8 and a color according to Hazen of 116. The final shampoo formulation was neutralized with 0.4 parts of a 20% solution of citric acid in water to a final pH value of 6.5.

The shampoo formulation exhibited no microbiological growth upon incubation at 25+/−2° C. for 7, 14 and 28 days after inoculation with 1.0% of a suspension of microorganisms with a titer of $10^4$ KBE/ml, comprising *Aspergillus niger*, and *Penicillium funiculosum*.

Example 15

A shampoo formulation was prepared as in Example 14 with 5 parts of the unpreserved silicone microemulsion according to Example 2, comprising 20% of Silicone Quaternium-18, 10% of a mixture of nonionic surfactants.

To 95 parts of this shampoo formulation were added
0.9 parts (0.9%) 2-phenoxyethanol (component a)),
3.0 parts (3.0%) 2-butyl-2-ethyl-1,3-propanediol (component b)),
0.1 parts (0.1%) ethylhexyl glycerin (component c)), and
1.0 parts (1.0%) 1,3-propanediol (component c)) and thoroughly mixed. The final shampoo formulation was neutralized with 0.4 parts of a 20% solution of citric acid in water to a final pH value of 6.5.

The shampoo formulation exhibited no microbiological growth upon incubation at 25+/−2° C. for 7, 14 and 28 days after inoculation with 1.0% of the suspension of microorganisms used in Example 14.

Example 16

A shampoo formulation was prepared as in Example 14 with 5 parts of the unpreserved silicone microemulsion according to Example 2, comprising 20% of Silicone Quaternium-18, and 10% of a mixture of nonionic surfactants.

To 95 parts of this shampoo formulation were added
1.0 parts (1.0%) 3-phenyl-1-propanol (component a)),
1.5 parts (1.5%) 2-butyl-2-ethyl-1,3-propanediol (component b)),
1.5 parts (1.5%) 2-methyl-2,4-hexanediol (component b)) and
1.0 parts (1.0%) 1,3-propanediol (component c)). The final shampoo formulation was neutralized with 0.4 parts of a 20% solution of citric acid in water to a final pH value of 6.5.

The shampoo formulation exhibited minor microbiological growth upon incubation at 25+/−2° C. for 7 days but no microbiological growth upon incubation for 14 and 28 days after inoculation with 1.0% of the suspension of microorganisms used in Example 14.

Comparative Example 11

A shampoo formulation was prepared as in Example 14 with 5 g of the unpreserved silicone microemulsion according to Example 2, comprising 20% of Silicone Quaternium-18, 10% of a mixture of nonionic surfactants, and water. To 96.75 parts of this shampoo formulation was added 3.25 parts 2-phenoxyethanol (component a)), but no component b), and thoroughly mixed. The final shampoo formulation was neutralized with 0.4 parts of a 20% solution of citric acid in water to a final pH value of 6.5.

The shampoo formulation exhibited strong to moderate microbiological growth upon incubation at 25+/−2° C. for 7 and 14, but no microbiological growth upon incubation for 24 days, after inoculation with 1.0% of the suspension of microorganisms used in Example 14.

Comparative Example 12

A shampoo formulation was prepared as in Example 14 with 5 g of the unpreserved silicone microemulsion according to Example 2, comprising 20% of Silicone Quaternium-18, 10% of a mixture of nonionic surfactants, and water. To 96.7 parts of this shampoo formulation were added
2.5 parts (2.5%) 2-butyl-2-ethyl-1,3-propanediol component b)),
0.75 parts (0.75%) 2-methyl-2,4-hexanediol (component b)) and
0.05 parts (0.05%) 1,3-propanediol (component c)),
but no component (a), and mixed until homogeneous. The final shampoo formulation was neutralized with 0.4 parts of a 20% solution of citric acid in water to a final pH value of 6.5.

The shampoo formulation exhibited strong to moderate microbiological growth upon incubation at 25+/−2° C. for 7, 14 and 28 days after inoculation with 1.0% of the suspension of microorganisms used in Example 14.

Tables

TABLE 1

| | Example | | | | | | | | | | |
|---|---|---|---|---|---|---|---|---|---|---|---|
| | 1 | C1 | 2 | C2 | C3 | 3 | 4 | C4 | 5 | C5 | C6 |
| Component a) | | | | | | | | | | | |
| PE | 0.9 | 0.9 | 3.3 | 4.3 | | | 0.9 | 0.9 | 0.9 | 0.9 | |
| PP | | | | | | 1.00 | | | | | |
| Component b) | | | | | | | | | | | |
| BEPD | 1.5 | | 1.0 | | 4.3 | 3.3 | 3.1 | | 2.0 | | 2.0 |
| MPPD | | | | | | | 1.0 | | | | |
| Component c) | | | | | | | | | | | |
| EHG | 0.6 | 0.6 | | | | | | 2.1 | 1.1 | 1.1 | 1.1 |
| OD | | | | | | | | 2.0 | | | |
| MPD | | | | | | | | | 0.5 | 0.5 | 0.5 |
| PD | | | | | | | | | 0.5 | 0.5 | 0.5 |
| Sum a)-c) | 3.0 | 1.5 | 4.3 | 4.3 | 4.3 | 4.3 | 5.0 | 5.0 | 5.0 | 3.0 | 4.1 |
| 1 week | | XX | XXX | XXX | XX | 0 | X | X | XXX | XXX | |
| 2 week | 0 | XX | 0 | XX | XXX | 0 | 0 | XX | 0 | XX | XXX |
| Days to destruction | <14 | >28 | 14 | 28 | >42 | <14 | <7 | >24 | 14 | >28 | >28 |

Component additives:
PE = 2-phenoxyethanol,
PP = 3-phenyl-1-propanol,
BEPD = 2-butyl-2-ethyl-1,3-propanediol,
DMPD = 2,2-dimethyl-1,3-propanediol,
MPPD = 2-methyl-2-propyl-1,3-propanediol,
EHG = ethylhexylglycerin,
OD, 1,2-octanediol,
DD = 1,2-dodecanediol,
MPD = 2-methyl-1,3-propanediol,
PD = 1,3-propanediol.
HG = 2-methyl-2,4-hexanediol
0 = no growth;
X = minimal growth (<5 colonies);
XX = moderate growth (5-10 colonies);
XXX = strong growth (>10 colonies)

TABLE 2

| | Example | | | | | | | | |
|---|---|---|---|---|---|---|---|---|---|
| | 6 | 7 | 8 | 9 | C7 | C8 | C9 | C10 | 10 |
| Component a) | | | | | | | | | |
| PE | 0.9 | 0.9 | 0.9 | 2.0 | 2.5 | | 0.9 | 0.9 | 0.9 |
| PP | | | | | | | | | |
| Component b) | | | | | | | | | |
| BEPD | 3.1 | 2 | 1.6 | | | 2.5 | | | 3.0 |
| DMPD | 1.0 | | | | | | | | |
| HG | | | | 0.50 | | | | | |
| Component c) | | | | | | | | | |
| EHG | | 1.1 | | | | | 1.1 | 1.75 | 0.6 |
| OD | | | | | | | | 2.35 | |
| PD | | | | | | | | | 0.5 |
| Sum a)-c) | 5.0 | 4.0 | 2.5 | 2.5 | 2.5 | 2.5 | 2.0 | 5.0 | 5.0 |
| 1 week | 0 | XX | XX | XX | XXX | XXX | | XXX | 0 |
| 2 week | 0 | X | X | 0 | XX | XXX | XXX | XXX | 0 |
| Days to destruction | <7 | 24 | 36 | 14 | 24 | >24 | >36 | 36 | <7 |

TABLE 3

| | Example | | |
|---|---|---|---|
| | 11 | 12 | 13 |
| Component a) | | | |
| PE | 0.9 | 0.9 | 0.9 |
| PP | | | |
| Component b) | | | |
| BEPD | | | 1.0 |
| DMPD | 1.5 | | |
| MPPD | 1.5 | | |
| HG | | 3 | |
| Component c) | | | |
| EHG | 0.6 | 0.6 | 0.1 |
| PD | 0.5 | 0.5 | |
| Sum a)-c) | 5.0 | 5.0 | 2.0 |
| 1 week | 0 | | |
| 2 week | 0 | 0 | 0 |
| Days to destruction | <7 | <14 | <14 |

TABLE 4

| | Example | | | | |
|---|---|---|---|---|---|
| | 14 | 15 | 16 | C11 | C12 |
| Component a) | | | | | |
| PE | | 0.9 | | 3.25 | |
| PP | 1.0 | | 1.0 | | |
| Component b) | | | | | |
| BEPD | 2.0 | 3.0 | 1.5 | | 2.5 |
| HG | | | 1.5 | | 0.75 |
| Component c) | | | | | |
| EHG | | 0.1 | | | |
| PD | | 1.0 | 1.0 | | 0.05 |
| Sum a)-c) | 3.0 | 5.0 | 5.0 | 3.25 | 3.3 |
| 1 week | 0 | 0 | X | XXX | XXX |
| 2 week | 0 | 0 | 0 | XX | XXX |
| Days to distruction | <7 | <7 | 14 | 24 | >24 |

The invention claimed is:

1. An aqueous composition comprising one or more silicones, and a) at least one compound of the general formula (1)

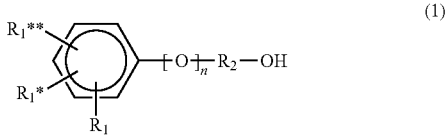

wherein n is 0 or 1, $R_1$, $R_1^*$ and $R_1^{**}$ are independently selected from the group consisting of hydrogen, a linear or branched C1-C9 alkyl group, and a linear or branched C1-C9 alkyloxy group, and $R_2$ is a linear or branched divalent C2-C5 alkyl group, and b) at least one compound selected from general formula (2)

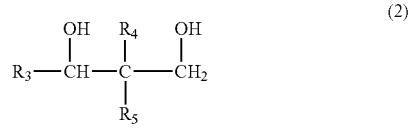

wherein compound (2) has 5 to 22 carbon atoms, and wherein $R_3$ is selected from the group consisting of hydrogen, a linear or branched C1 to C12 alkyl group, a linear or branched C1 to C12 alkylaryl group, an aryl group, a linear or branched C1 to C12 alkyloxy group, a linear or branched C1 to C12 alkylaryloxy group, and an aryloxy group, and $R_4$ and $R_5$ are the same or different and are selected from the group consisting of a linear or branched C1 to C12 alkyl group, a linear or branched C1 to C12 alkylaryl group, an aryl group, or $R_4$ and $R_5$ together form an optionally substituted ring system with at least 5 carbon atoms, and c) optionally one or more compounds selected from the group consisting of the general formulae (4) and (5)

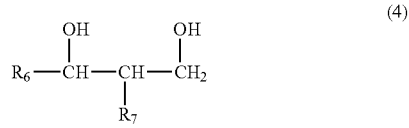

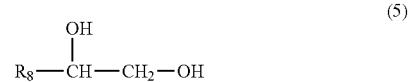

wherein $R_6$ and $R_7$ are either both hydrogen or one is a methyl group and the other is hydrogen and $R_8$ is selected from the group consisting of a linear or branched C6 to C14 alkyl group, a linear or branched C6 to C14 alkyloxy group, a linear or branched C6 to C14 alkyloxyalkyl group, a linear or branched C6 to C14 alkylaryl, a linear or branched C6 to C14 alkylaryloxy and aryloxy group.

2. The aqueous composition according to claim 1, comprising d) one or more substances selected from the group consisting of i) nonionic surfactants,
ii) cationic surfactants,
iii) anionic surfactants,
iv) amphoteric surfactants,
v) fatty oils and fats with between 8 and 32 carbon atoms,
vi) organic acids and polymeric derivatives thereof,
vii) inorganic or polymeric thickeners,
viii) antioxidants, and
ix) pH adjusting agents.

3. The aqueous composition according to claim 1, comprising at least one surfactant.

4. The aqueous composition according to claim 1, comprising components a) and b) in a quantity producing a synergistic antimicrobial effect.

5. The aqueous composition according to claim 1, wherein the total weight of the sum of the components a), b) and c) is from 0.5 to 12 weight based on the total weight of the aqueous composition.

6. The aqueous composition according to claim 1, wherein the amount of the one or more silicones is in the range of 1 and 50 weight-%, based on the total weight of the aqueous composition.

7. The aqueous composition according to claim 1, wherein the silicones are selected from the group consisting of polyorganosiloxanes which optionally may have one or more functional groups and mixtures thereof.

8. The aqueous composition according to claim 1, comprising 0.1 to 5.0 weight-%, of the total weight of the components a) based on the total weight of the aqueous composition, and said component a).

9. The aqueous composition according to claim 1, comprising 0.1 to 5.0 weight-% of the total weight of the components b) based on the total weight of the aqueous composition, and said component b) is selected from the group consisting of 2-methyl-2,4-pentanediol, 2-methyl-2,4-hexanediol, 2,2-dimethyl-1,3-propanediol, 2-methyl-2-propyl-1,3-propanediol, 2,2-dibutyl-1,3-propanediol, 2-butyl-2-ethyl-1,3-propanediol and 2,2-dioctyl-1,3-propanediol, and mixtures thereof.

10. The aqueous composition according to claim 1, comprising 0.1 to 5.0 weight-%, of the total weight of the components c) based on the total weight of the aqueous composition, and said component c) is preferably selected from the group consisting of 1,2-octanediol, 1,2-decanediol, 3-(2-ethylhexyloxy)-1,2-propanediol, 1,2-dodecanediol, 2-methyl-1,3-propanediol, 1,3-propanediol and 1,3-butanediol, and mixtures thereof.

11. An article selected from the group consisting of homecare articles, household articles, industrial articles, fabric articles, cosmetic articles, hygienic articles, personal care articles and medical articles wherein the article comprises the aqueous composition according to claim 1.

12. The article according to claim 11, wherein the aqueous composition further comprises e) one or more functional components, selected from the group consisting of:
   i) volatile silicone compounds,
   ii) anionic, nonionic, cationic or amphoteric surfactants,
   iii) oily phase-forming substance,
   iv) saturated and unsaturated aliphatic alcohols, which are different from components a), b) and c) of the aqueous composition,
   v) organic acids and polymeric derivatives thereof,
   vi) antioxidants,
   vii) UV absorbers,
   viii) perfumes and fragrances,
   ix) dyes and pigments,
   x) hydrophilic components or polymers,
   xi) emollients,
   xii) organic polymeric quaternary ammonium compounds,
   xiii) antidandruff agents,
   xiv) antiperspirants,
   xv) insect repellants,
   xvi) vitamins or vitamin precursors,
   xvii) botanical extracts,
   xviii) inorganic or polymeric thickeners,
   xix) additional components with antimicrobiological properties, which are different from components a), b) and c) as defined in the aqueous composition,
   xx) silicone and organic polymer fixatives, and
   xxi) organic solvents.

13. A method of preserving aqueous compositions, comprising at least one silicone, against microorganisms, which comprises admixing said aqueous composition comprising the at least one silicone, with a mixture of components a) and b), and optionally component c), as defined in claim 1.

14. A preservative composition comprising the aqueous composition of claim 1.

15. The aqueous composition according to claim 1, wherein the total weight of the sum of the components a), b) and c) is from 1.5 to 5.0 wt.-%, based on the total weight of the aqueous composition.

16. The aqueous composition according to claim 1, wherein the amount of the one or more silicones is in the range of 10 and 30 weight-%, based on the total weight of the aqueous composition.

17. The aqueous composition according to claim 1, wherein the silicones are selected from the group consisting of polydimethylsiloxanes, amino group-modified silicones, polyether group-modified silicones, and silicones comprising at least one quaternary ammonium group, and mixtures thereof.

18. The aqueous composition according to claim 1, comprising 0.1 to 2.0 weight-% of the total weight of the components a) based on the total weight of the aqueous composition, and said component a) is 2-phenoxyethanol and/or 3-phenyl-1-propanol.

19. The aqueous composition according to claim 1, comprising 0.1 to 3.0 weight-%, of the total weight of the components b) based on the total weight of the aqueous composition, and said component b) is selected from 2-butyl-2-ethyl-1,3-propanediol, 2-methyl-2,4-hexanediol, or 2-methyl-2-propyl-1,3-propanediol, and combinations thereof.

20. The aqueous composition according to claim 1, comprising 0.1 to 3.0 weight-%, of the total weight of the components c) based on the total weight of the aqueous composition, and said component c) is selected from (3-(2-ethylhexyloxy)-1,2-propanediol, 1,3-propanediol, 1,2-dodecanediol, or 2-methyl-1,3-propanediol, and combinations thereof.

21. The aqueous composition according to claim 1, wherein compound (2) has 6 to 22 carbon atoms.

22. An oil-in-water emulsion comprising 5 and 40 weight-% of one or more silicones based on the weight of the oil-in-water emulsion, and
   a) at least one compound of the general formula (1)

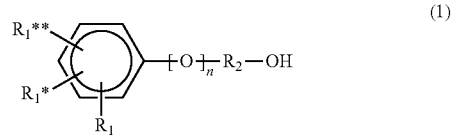

wherein
n is 0 or 1,
$R_1$, $R_1^*$ and $R_1^{**}$ are independently selected from the group consisting of hydrogen, a linear or branched C1-C9 alkyl group, and a linear or branched C1-C9 alkyloxy group, and
$R_2$ is a linear or branched divalent C2-C5 alkyl group, and
b) at least one compound selected from the group consisting of the general formulae (2) and (3)

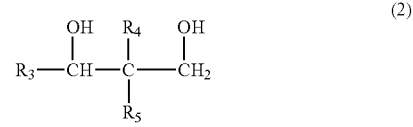

wherein compounds (2) has 5 to 22 carbon atoms, and wherein
$R_3$ is selected from the group consisting of hydrogen, a linear or branched C1 to C12 alkyl group, a linear or branched C1 to C12 alkylaryl group, an aryl group, a linear or branched C1 to C12 alkyloxy group, a linear or branched C1 to C12 alkylaryloxy group, and an aryloxy group, and
$R_4$ and $R_5$ are the same or different and are selected from the group consisting of a linear or branched C1 to C12 alkyl group, a linear or branched C1 to C12 alkylaryl group, an aryl group, or $R_4$ and $R_5$ together form an optionally substituted ring system with at least 5 carbon atoms, and c) optionally one or more compounds selected from the group consisting of the general formulae (4) and (5)

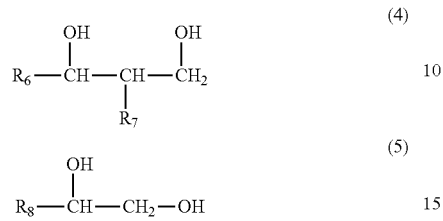

(4)

(5)

wherein $R_6$ and $R_7$ are either both hydrogen or one is a methyl group and the other is hydrogen and $R_8$ is selected from the group consisting of a linear or branched C6 to C14 alkyl group, a linear or branched C6 to C14 alkyloxy group, a linear or branched C6 to C14 alkyloxyalkyl group, a linear or branched C6 to C14 alkylaryl, a linear or branched C6 to C14 alkylaryloxy and aryloxy group.

23. The aqueous composition according to claim 22, wherein compound (2) has 6 to 22 carbon atoms.

* * * * *